United States Patent
O'Connor et al.

(10) Patent No.: US 8,216,631 B2
(45) Date of Patent: *Jul. 10, 2012

(54) HEART VALVE PROSTHESIS AND METHOD OF MANUFACTURE

(75) Inventors: Bernard O'Connor, South Lanarkshire (GB); David John Wheatley, Glasgow (GB); Gillian Maureen Bernacca, Glasgow (GB); William Stafford Haworth, Biggar (GB)

(73) Assignee: Aortech International PLC, Surrey (GB)

( * ) Notice: Subject to any disclaimer, the term of this patent is extended or adjusted under 35 U.S.C. 154(b) by 0 days.

This patent is subject to a terminal disclaimer.

(21) Appl. No.: 12/939,848

(22) Filed: Nov. 4, 2010

(65) Prior Publication Data

US 2011/0049757 A1 Mar. 3, 2011

Related U.S. Application Data

(60) Division of application No. 11/512,847, filed on Aug. 30, 2006, now Pat. No. 7,833,565, which is a continuation of application No. 10/165,204, filed on Jun. 6, 2002, now abandoned, which is a continuation-in-part of application No. PCT/GB00/04673, filed on Dec. 7, 2000.

(30) Foreign Application Priority Data

Dec. 8, 1999 (GB) .................................. 9928905.0
Jun. 13, 2001 (GB) .................................. 0114345.2

(51) Int. Cl.
*A61L 33/00* (2006.01)

(52) U.S. Cl. ......... 427/2.24; 427/2.1; 427/133; 427/135
(58) Field of Classification Search ................. 427/2.25, 427/2.24, 133, 135
See application file for complete search history.

(56) References Cited

U.S. PATENT DOCUMENTS

| 4,222,126 A | 9/1980 | Boretos et al. |
| 4,265,694 A | 5/1981 | Boretos et al. |
| 4,364,127 A | 12/1982 | Pierce et al. |
| 4,888,009 A | 12/1989 | Lederman et al. |
| 5,358,518 A | 10/1994 | Camilli |

(Continued)

FOREIGN PATENT DOCUMENTS

WO    WO 97/41808    11/1997

(Continued)

OTHER PUBLICATIONS

Bernacca et al., "In vitro Function and Durability of a Polyurethane Heart Valve: Material Considerations," J. Heart Valve Dis., 5(5):538-542 (Sep. 1996).

(Continued)

*Primary Examiner* — Dah-Wei Yuan
*Assistant Examiner* — Andrew Bowman
(74) *Attorney, Agent, or Firm* — Popovich, Wiles & O'Connell, P.A.

(57) ABSTRACT

A cardiac valve prosthesis having a frame and two or more leaflets (preferably three) attached to the frame. The leaflets are attached to the frame between posts, with a free edge which can seal the leaflets together when the valve is closed under back pressure. The leaflets are created in a mathematically defined shape allowing good wash-out of the whole leaflet orifice, including the area close to the frame posts, thereby relieving the problem of thrombus deposition under clinical implant conditions.

20 Claims, 13 Drawing Sheets

U.S. PATENT DOCUMENTS

| | | | |
|---|---|---|---|
| 5,376,113 | A | 12/1994 | Jansen et al. |
| 5,500,016 | A | 3/1996 | Fisher |
| 5,562,729 | A | 10/1996 | Purdy et al. |
| 5,800,527 | A | 9/1998 | Jansen et al. |
| 6,165,215 | A | 12/2000 | Rottenberg et al. |
| 6,283,994 | B1 | 9/2001 | Moe et al. |
| 6,283,995 | B1 | 9/2001 | Moe et al. |
| 6,881,224 | B2 | 4/2005 | Kruse et al. |
| 7,833,565 | B2 * | 11/2010 | O'Connor et al. ............ 427/2.1 |

FOREIGN PATENT DOCUMENTS

| | | |
|---|---|---|
| WO | WO 98/32400 | 7/1998 |
| WO | WO 00/62716 | 10/2000 |
| WO | WO 01/41679 A1 | 6/2001 |

OTHER PUBLICATIONS

Bernacca et al., "Polyurethane Heart Valves: Fatigue Failure, Calcification and Polyurethane Structure," J. Biomed. Mater. Res., 34(3):371-379 (Mar. 5, 1997).

Bernacca et al., "Polyurethane Heart Valve Durability: Effects of Leaflet Thickness," Int J Artif Organs, 20(6):327-331 (Jun. 1997).

Bernacca et al., "Durability and Function of a Polyurethane Heart Valve After Six Months in vivo," Presented at the XII World Congress of International Society for Artificial Organs and XXVI Congress of the European Society for Artificial Organs, Edinburgh, Aug. 1999, Artificial Organs, vol. 23, No. 7 (Jul. 1999).

Mackay et al., "New Polyurethane Heart Valve Prosthesis: Design, Manufacture and Evaluation," Biomaterials, 17(19):1857-1863 (1996).

Mackay et al., "In vitro Function and Durability Assessment of a Polyurethane Heart Valve Prosthesis," Artificial Organs, 20(9):1017-1025 (Sep. 1996).

Wheatley et al., "Polyurethane: Material for the Next Generation of Heart Valve Prostheses?" Eur. J. Cardio-Thorac. Surg., 17(4):440-448 (Apr. 2000).

International Search Report of PCT/GB00/04673 (4 pages).

Search Report for Counterpart International Application No. PCT/GB02/02409 (5 pages).

* cited by examiner

HEART VALVE PROSTHESIS AND METHOD OF MANUFACTURE

This application is a divisional of U.S. application Ser. No. 11/512,847, filed Aug. 30, 2006, which is a continuation of U.S. application Ser. No. 10/165,204, filed Jun. 6, 2002, the contents of each of which are hereby incorporated herein by reference, which is a continuation in part of International Application Serial No. PCT/GB00/04673, filed Dec. 7, 2000, which International Application was published by the International Bureau in English as WO 01/41679 on Jun. 14, 2001.

FIELD OF THE INVENTION

The present invention relates to medical implants, particularly cardiac and vascular implants and prostheses. More specifically, the invention relates to a cardiac valve prosthesis comprising a frame and leaflets. Such valves may also be made without rigid frames and may also be used as valves in artificial hearts, whether the latter are intended for permanent implantation or for temporary support of a patient.

BACKGROUND OF THE INVENTION

In mammals the heart is the organ responsible for maintaining an adequate supply of blood, and hence of oxygen and nutrients, to all parts of the body. Reverse flow of blood through the heart is prevented by four valves which serve as the inlet and outlet of each of the two ventricles, the pumping chambers of the heart.

Dysfunction of one or more of these valves can have serious medical consequences. Such dysfunction may result from congenital defects, or from disease induced damage. Forms of dysfunction include stenosis (reduction in the orifice of the open valve) and regurgitation (reverse flow through the closing or closed valve), either of which increases the work required by the heart to maintain the appropriate blood flows to the body.

In many cases the only effective solution is to replace the malfunctioning valve. A valve replacement operation is expensive and requires specialised facilities for open heart surgery. Replacement of failed artificial heart valves carries increased risk over the initial replacement, so there are practical limits on the number of times reoperation can be undertaken. Consequently, the design and materials of an artificial valve must provide for durability of the valve in the patient. The artificial valve must also operate without high pressure gradients or undue reverse flow during closing or when closed, because these are the very reasons for which a replacement of the natural valve is undertaken.

Mechanical valves, which use a ball or a disc or a pair of pivoting rigid leaflets as the opening member(s) can meet these combined requirements of hemodynamic performance and durability. Unfortunately, a patient who has had a mechanical valve implanted must be treated with anticoagulants, otherwise blood will clot on the valve. Clotting on the valve can either restrict the movement of the valve opening member(s), impairing valve function, or can break free from the valve and obstruct blood vessels downstream from the valve, or both. A patient receiving a mechanical valve will be treated with anticoagulants for life.

Valves excised from pigs and treated with glutaraldehyde to crosslink and stabilise the tissue are also used for replacement of defective valves. These may be mounted on a more or less rigid frame, to facilitate implantation, or they may be unmounted and sewn by the surgeon directly to the vessel walls at operation. A further type of valve replacement is constructed from natural tissue, such as pericardium, treated with glutaraldehyde and mounted on a frame. Valves from pigs or made from other animal or human tissue are collectively known as tissue valves. A major advantage of tissue valves over mechanical valves is that they are much less likely to provoke the blood to clot, and so patients receiving tissue valves are not normally given anticoagulants other than during the immediate post operative period. Unfortunately, tissue valves deteriorate over time, often as a result of calcification of the crosslinked natural tissue. This deterioration presents a problem, particularly in young patients. Thus, although the recipient of a tissue valve is not required to take anticoagulants, the durability of tissue valves is less than that of mechanical valves.

In third world countries, where rheumatic fever is still common, the problems of valve replacement in young patients are considerable. Anticoagulants, required for mechanical valves, are impractical and accelerated calcification of tissue valves precludes their use.

In the Western world, life expectancy continues to increase, and this results in a corresponding rise both in patients requiring cardiac valve replacement, and in those patients needing replacement of deteriorating artificial valves implanted in the past. There is, therefore, a need for a replacement heart valve with good hemodynamics, extended durability and having sufficiently low risk of inducing clotting so that anticoagulants are not necessary.

The natural heart valves use thin flexible tissue leaflets as the closing members. The leaflets move readily out of the orifice as blood begins to flow through the valve so that flow through the open valve is unrestricted by the leaflets. Tissue valves function similarly, providing a relatively unrestricted orifice when the valve is open. For mechanical valves, on the other hand, the closing member rotates in the orifice, but is not removed from the orifice when the valve opens. This provides some restriction to flow, but more importantly, disturbs the blood flow patterns. This disturbance to the flow is widely held to initiate, or at least to contribute significantly to, the observed tendency of mechanical valves to produce clotting.

A number of trileaflet polyurethane valve designs have been described.

A valve design, comprising a leaflet geometry which was elliptical in the radial direction and hyperbolic in the circumferential direction in the closed valve position, with leaflets dip-coated from non-biostable polyurethane solutions onto injection-molded polyurethane frames has attained durabilities in excess of 800 million cycles during in vitro fatigue testing (Mackay T G, Wheatley D J, Bernacca G M, Hindle C S, Fisher A C. New polyurethane heart valve prosthesis: design, manufacture and evaluation. *Biomaterials* 1996; 17:1857-1863; Mackay T G, Bernacca G M, Wheatley D J, Fisher A C, Hindle C S. In vitro function and durability assessment of a polyurethane heart valve prosthesis. *Artificial Organs* 1996; 20:1017-1025; Bernacca G M, Mackay T G, Wheatley D J. In vitro function and durability of a polyurethane heart valve: material considerations. *J Heart Valve Dis* 1996; 5:538-542; Bernacca G M, Mackay T G, Wilkinson R, Wheatley D J. Polyurethane heart valves: fatigue failure, calcification and polyurethane structure. *J Biomed Mater Res* 1997; 34:371-379; Bernacca G M, Mackay T G, Gulbransen M J, Donn A W, Wheatley D J. Polyurethane heart valve durability: effects of leaflet thickness. *Int J Artif Organs* 1997; 20:327-331). However, this valve design became unacceptably stenotic in small sizes. Thus, a redesign was effected, changing the hyperbolic angle from the free edge to the leaflet base, and replacing the injection-molded frame with a rigid, high modulus polymer frame. This redesign permitted the use of a thinner frame, thus increasing valve orifice area. This valve design, with a non-biostable polyurethane leaflet material, was implanted in a growing sheep model. Valve performance was good over the six month implant period, but the region close to the frame posts on the inflow side of the valve, at which full leaflet opening was not achieved, suffered a local accumulation of thrombus (Bernacca G M, Raco L, Mackay T G, Wheatley D J. Durability and function of a polyurethane heart valve after six months in vivo. Presented at the XII World Congress of International Society for Artificial Organs and XXVI Congress of the European Society for Artificial Organs, Edinburgh, August 1999. Wheatley D J, Raco L, Bernacca G M, Sim I, Belcher P R, Boyd J S. Polyurethane: material for the next generation of heart valve prostheses? Eur. J. Cardio-Thorac. Surg. 2000; 17; 440-448). This valve design used non-biostable polyurethane, which had tolerable mechanical durability, but which showed signs of polymer degradation after six months in vivo.

International Patent Application WO 98/32400 entitled "Heart Valve Prosthesis" discloses a similar design, i.e., closed leaflet geometry, comprising essentially a trileaflet valve with leaflets molded in a geometry derived from a sphere towards the free edge and a cone towards the base of the leaflets. The spherical surface, defined by its radius, is intended to provide a tight seal when the leaflets are under back pressure, with ready opening provided by the conical segment, defined by its half-angle, at the base of the leaflets. Were the spherical portion located at the leaflet base it is stated that this would provide an advantage in terms of the stress distribution when the valve is closed and under back pressure.

U.S. Pat. No. 5,376,113 (Jansen et al.) entitled "Closing Member Having Flexible Closing Elements, Especially a Heart Valve" issued Dec. 27, 1994 to Jansen et al. discloses a method of producing flexible heart valve leaflets using leaflets attached to a base ring with posts extending from this upon which the leaflets are mounted. The leaflets are formed with the base ring in an expanded position, being effectively of planar sheets of polymer, which become flaccid on contraction of the ring. The resulting valve is able to maintain both a stable open and a stable closed position in the absence of any pulsatile pressure, though in the neutral unloaded position the valve leaflets contain bending stresses. As a consequence of manufacturing the valve from substantially planar sheets, the included angle between the leaflets at the free edge where they attach to the frame is 60° for a three leaflet valve.

U.S. Pat. No. 5,500,016 (Fisher) entitled "Artificial Heart Valve" discloses a valve having a leaflet shape defined by the mathematical equation $z^2+y^2=2RL(x-g)-\alpha(x-g)^2$, where g is the offset of the leaflet from the frame, RL is the radius of curvature of the leaflet at (g,0,0) and $\alpha$ is the shape parameter and is >0 and <1.

A valve design having a partially open configuration when the valve is not subject to a pressure gradient, but assuming a fully-open position during forward flow is disclosed in International Patent Application WO 97/41808 entitled "Method for Producing Heart Valves". The valve may be a polyurethane trileaflet valve and is contained within a cylindrical outer sleeve.

U.S. Pat. Nos. 4,222,126 (Boretos et al.) and 4,265,694 (Boretos et al.) disclose a trileaflet polyurethane valve with integral polyurethane elastomeric leaflets having their leading edges reinforced with an integral band of polymer and the leaflets reinforced radially with thicker lines of polyurethane.

The problem of chronic thrombus formation and tissue overgrowth arising from the suture ring of valves has been addressed by extension of the valve body on either side of the suture ring as disclosed in U.S. Pat. No. 4,888,009 (Lederman et al.) entitled "Prosthetic Heart Valve".

Current polyurethane valve designs have a number of potential drawbacks. Close coaptation of leaflets, while ensuring good valve closure, limits the wash-out of blood during hemodynamic function, particularly in the regions close to the stent posts at the commissures. This region of stagnation is likely to encourage local thrombogenesis, with further restriction of the valve orifice in the longer term as well as increasing the risk of material embolising into the circulation. Associated with the thrombosis may be material degradation (in non-biostable polyurethanes) and calcification resulting in localised stiffening the leaflets, stress concentrations and leaflet failure. As previously discussed, animal implants of a trileaflet polyurethane valve design have indicated that thrombus does tend to collect in this region, restricting the valve orifice and damaging the structure of the valve.

Present valve designs are limited by the availability of suitable polyurethanes which possess good mechanical properties as well as sufficient durability to anticipate clinical functionality of up to twenty years or more. Many low modulus materials, which provide good hydrodynamic function, fail during fatigue testing at unacceptably low durations, due to their greater susceptibility to the effects of accumulated strain. Higher modulus polyurethanes may be better able to withstand repeated stress without accumulating significant damage, but are too stiff to provide good hydrodynamic function in conventional almost-closed geometry valve designs. Current design strategies have not been directed towards enabling the incorporation of potentially more durable, higher modulus leaflet materials, nor the creation of a valve design that is able to maintain good hydrodynamic function with low modulus polyurethanes manufactured as thick leaflets.

The nature of the valve leaflet attachment to the frame is such that, in many valve designs, there is a region of leaflet close to the frame, which is restrained by the frame. This region may extend some distance into the leaflet before it interfaces with the free-moving part of the leaflet, or may be directly at the interface between frame and leaflet. There thus exists a stress concentration between the area of leaflet that is relatively mobile, undergoing transition between fully open and fully closed, and the relatively stationary commissural region. The magnitude of this flexural stress concentration is maximized when the design parameters predicate high bending strains in order for the leaflet to achieve its fully open position.

U.S. Pat. Nos. 4,222,126 (Boretos et al.) and 4,265,694 (Boretos et al.) disclose a valve which uses thickened leaflet areas to strengthen vulnerable area of the leaflets. However this approach is likely to increase the flexure stress and be disadvantageous in terms of leaflet hydrodynamic function.

The major difficulties which arise in designing synthetic leaflet heart valves can be explained as follows. The materials from which the natural trileaflet heart valves (aortic and pulmonary) are formed have deformation characteristics particularly suited to the function of such a valve. Specifically, they have a very low initial modulus, and so they are very flexible in bending, which occurs at low strain. This low modulus also allows the leaflet to deform when the valve is closed and loaded in such a way that the stresses generated at the attachment of the leaflets, the commissures, are reduced. The leaflet material then stiffens substantially, and this allows the valve to sustain the closed loads without prolapse. Synthetic materials with these mechanical properties are not available.

Polyurethanes can be synthesized with good blood handling and good durability. They are available with a wide range of mechanical properties, although none has as low a modulus as the natural heart valve material. Although they show an increase in modulus at higher strains, this does not occur until strains much higher than those encountered in leaflet heart valves.

Polyurethanes have been the materials of choice for synthetic leaflet heart valves in the last decade or more. More recently, polyurethanes have become available which are resistant to degradation when implanted. They are clearly more suitable for making synthetic leaflet heart valves than non-stable polyurethanes, but their use suffers from the same limitations resulting from their mechanical properties. Therefore, design changes must be sought which enable synthetic trileaflet heart valves to function with the best available materials.

Key performance parameters which must be considered when designing a synthetic leaflet heart valve include pressure gradient, regurgitation, blood handling, and durability.

To minimize the gradient across the open valve, the leaflets must open wide to the maximum orifice possible, which is defined by the inside diameter of the stent. This means that there must be adequate material in the leaflets so they can be flexed into a tube of diameter equal to the stent internal diameter. In addition, there has to be a low energy path for this bending because the pressure forces available to open the valve are small, and the lower the gradient, the smaller the pressure becomes. All the leaflets must open for the lowest cardiac output likely to be encountered by that valve in clinical service.

To minimize closing regurgitation (reverse flow lost through the closing valve) the valve leaflets must be produced at or close to the closed position of the valve. To minimize closed valve regurgitation (reverse flow through the valve once it has closed), the apposition of the leaflets in the commissural region is found to be key, and from this perspective the commissures should be formed in the closed position.

Proper blood handling means minimising the activation both of the coagulation system and of platelets. The material of construction of the valve is clearly a very important factor, but flow through the valve must also avoid exposing blood either to regions of high shear (velocity gradient) or to regions of relative stasis. Avoiding regions of high shear is achieved if the valve opens fully, and relative stasis is avoided if the leaflet/frame attachment and the commissural region in particular opens wide. This is not achieved with typical synthetic materials when the commissures are molded almost closed, because the stiffness of synthetics is too high.

Durability depends to a large extent on the material of construction of the valve leaflets, but for any given material, lifetime will be maximized if regions of high stress are avoided. The loads on the closed valve are significantly greater than loads generated during valve opening. Therefore, the focus should be on the closed position. Stresses are highest in the region of the commissures where loads are transmitted to the stent, but they are reduced when the belly of the leaflet is as low as practicable in the closed valve. This means that there must be sufficient material in the leaflet to allow the desired low closing.

SUMMARY OF THE INVENTION

The present invention provides a cardiac valve prosthesis comprising a frame and two or more leaflets (preferably three) attached to the frame. Two embodiments of the invention are disclosed.

1. First Embodiment

The leaflets are attached to the frame between posts, with a free edge which can seal the leaflets together when the valve is closed under back pressure. The leaflets are created in a mathematically defined shape allowing good wash-out of the whole leaflet orifice, including the area close to the frame posts, thereby relieving the problem of thrombus deposition under clinical implant conditions.

The leaflet shape has a second design feature, by which the pressure required to open the valve and the pressure gradient across the valve in the open position is reduced by creating a valve which is partially open in its stable unstressed position. Molding the leaflets in a partially open position permits them to open easily to a wider angle resulting in an increased effective orifice area, for any given polyurethane/elastomeric material. This permits the use of materials from a wider range of mechanical properties to fabricate the leaflets, including those of a relatively stiff nature, and also permits lower modulus materials to be incorporated as thicker and hence more durable leaflets, while retaining acceptable leaflet hydrodynamic function.

A third design feature is the reduction of a stress concentration in the vicinity of the commissural region of the leaflets. In many valve designs, there exists a region of localised high bending where the opening part of the flexible leaflet merges into the stationary region of the leaflet adjacent to the valve frame. The current design reduces the bending, and hence the local stress concentration, in this region. This feature is designed to enhance the valve durability.

The wide opening of the leaflet coaptation close to the stent posts improves blood washout, reduces thrombogenesis and minimizes embolic risks to the recipient, by allowing a clear channel for blood flow throughout the whole valve orifice.

The partially open design acts to reduce the fluid pressure required to open the valve. This in turn results in lower pressure gradients across the valve, allowing the use of durable, stiffer polyurethanes to fabricate the valve which may be better equipped to deal with a cyclic stress application or thicker leaflets of lower modulus polyurethanes, hence achieving good durability with good hydrodynamic function. The position of the leaflet in its stable unstressed state acts to reduce the stress concentration resulting from leaflet bending, hence increasing valve durability.

In one aspect the invention is a cardiac valve prosthesis comprising a frame defining a blood flow axis and at least two leaflets attached to the frame. The at least two leaflets are configured to be movable from an open to a closed position. The leaflets have a blood inlet side and a blood outlet side and are in the closed position when fluid pressure is applied to the outlet side, and in the open position when fluid pressure is applied to the inlet side. The leaflets are in a neutral position intermediate the open and closed position in the absence of fluid pressure being applied to the leaflets. The at least two leaflets include a first leaflet. The first leaflet has a surface contour such that an intersection of the first leaflet with at least one plane perpendicular to the blood flow axis forms a first composite wave. The first composite wave is substantially defined by a first wave combined with at least a second wave superimposed over the first wave. The first wave has a first frequency and the second wave has a second frequency, different from the first frequency. Alternatively, the first composite wave may be defined by a first wave combined with second and third waves superimposed over the first wave. The third wave has a third frequency which is different from the first frequency.

Both the first wave and the second wave may be symmetric or asymmetric about a plane parallel to and intersecting the blood flow axis and bisecting the first leaflet. The first composite wave may be symmetric or asymmetric about a plane parallel to and intersecting the blood flow axis and bisecting the first leaflet. The at least two leaflets may include second and third leaflets. An intersection of the second and third leaflets with a plane perpendicular to the blood flow axis forms second and third composite waves. The second and third composite waves are substantially the same as the first composite wave. The first and second waves may be defined by an equation which is trigonometric, elliptical, hyperbolic, parabolic, circular, a smooth analytic function or a table of values. The at least two leaflets may be configured such that they are substantially free of bending stresses when in the neutral position. The frame may be substantially cylindrical having first and second ends, one of the ends defining at least two scalloped edge portions separated by at least two posts, each post having a tip, and wherein each leaflet has a fixed edge joined to a respective scalloped edge portion of the frame and a free edge extending substantially between the tips of two posts. The first and second waves may be symmetric about a plane parallel to and intersecting the blood flow axis and bisecting the first leaflet or at least one of the first and second waves may be symmetric about such plane. The first leaflet may have a surface contour such that when the first leaflet is in the neutral position an intersection of the first leaflet with a plane parallel to and intersecting the blood flow axis and bisecting the first leaflet forms a fourth wave.

In another aspect the invention is a method of making a cardiac valve prosthesis. The valve prosthesis includes a frame defining a blood flow axis substantially parallel to the flow of blood through the valve prosthesis and at least two flexible leaflets attached to the frame. The method includes providing a forming element having at least two leaflet forming surfaces. The forming element is engaged with the frame. A coating is applied over the frame and engaged forming element. The coating binds to the frame. The coating over the leaflet forming surfaces forms the at least two leaflets. The at least two leaflets are configured to be movable from an open to a closed position. The leaflets have a blood inlet side and a blood outlet side and are in the closed position when fluid pressure is applied to the outlet side, and in the open position when fluid pressure is applied to the inlet side. The leaflets are in a neutral position intermediate the open and closed position in the absence of fluid pressure being applied to the leaflets. The at least two leaflets include a first leaflet. The first leaflet has a surface contour such that the intersection of the first leaflet with at least one plane perpendicular to the blood flow axis forms a first composite wave. The first composite wave is substantially defined by a first wave combined with a second superimposed wave. The first wave has a first frequency and the second wave has a second frequency different from the first frequency. After the coating is applied the forming element is disengaged from the frame. The first composite wave formed in the coating step may be defined by a first wave combined with second and third waves superimposed over the first wave. The third wave has a third frequency which is different from the first frequency.

The first and second waves formed in the coating step may be either symmetric or asymmetric about a plane parallel to and intersecting the blood flow axis and bisecting the first leaflet. The first composite wave formed in the coating step may be symmetric or asymmetric about a plane parallel to and intersecting the blood flow axis and bisecting the first leaflet. The at least two leaflets formed in the coating step may include second and third leaflets. An intersection of the second and third leaflets with a plane perpendicular to the blood flow axis forms second and third composite waves, respectively. The second and third composite waves are substantially the same as the first composite wave. The first and second waves formed in the coating step may be defined by an equation which is trigonometric, elliptical, hyperbolic, parabolic, circular, a smooth analytic function or a table of values.

The first and second waves in the coating step may be symmetric about a plane parallel to and intersecting the blood flow axis and bisecting the first leaflet or at least one of the first and second waves may be asymmetric about such plane. The at least two leaflets in the coating step are configured such that they are substantially free of bending stresses when in the neutral position.

In a further aspect the invention is a cardiac valve prosthesis comprising a frame defining a blood flow axis and at least two leaflets attached to the frame including a first leaflet. The first leaflet has an internal surface facing the blood flow axis and an external surface facing away from the blood flow axis. The first leaflet is configured such that a mean thickness of a first half of the first leaflet is different than a mean thickness of a second half of the first leaflet. The first and second halves are defined by a plane parallel to and intersecting the blood flow axis and bisecting the first leaflet. The first leaflet may be further configured such that a thickness of the first leaflet between the internal and external surfaces along a cross section defined by the intersection of a plane perpendicular to the blood flow axis and the first leaflet changes gradually and substantially continuously from a first end of the cross section to a second end of the cross section.

In another aspect the invention is a method of making a cardiac valve prosthesis which includes a frame defining a blood flow axis substantially parallel to the flow of blood through the valve prosthesis and at least two flexible leaflets attached to the frame. The method includes providing a mold having a cavity sized to accommodate the frame, inserting the frame into the mold, inserting the mold into an injection molding machine, and injecting molten polymer into the cavity of the mold to form the at least two leaflets. The injection of the molten polymer causes the at least two leaflets to bond to the frame. The cavity is shaped to form the at least two leaflets in a desired configuration. The at least two leaflets are configured to be movable from an open to a closed position. The leaflets have a blood inlet side and a blood outlet side and are in the closed position when fluid pressure is applied to the outlet side, and in the open position when fluid pressure is applied to the inlet side. The leaflets are in a neutral position intermediate the open and closed position in the absence of fluid pressure being applied to the leaflets. The at least two leaflets include a first leaflet having a surface contour such that when the first leaflet is in the neutral position an intersection of the first leaflet with at least one plane perpendicular to the blood flow axis forms a first composite wave. The first composite wave is substantially defined by a first wave combined with at least a second superimposed wave. The first wave may have a first frequency, the second wave may have a second frequency, the first frequency being different from the second frequency.

In a still further aspect the invention is a method of designing a cardiac valve prosthesis which includes a frame and at least two flexible leaflets attached to the frame. The method includes defining a first desired shape of the leaflets in a first position, defining a second desired shape of the leaflets in a second position different from the first position, and conducting a draping analysis to identify values of adjustable parameters defining at least one of the first and second shapes. The draping analysis ensures that the leaflets are comprised of a sufficient amount and distribution of material for the leaflets to assume both the first and second desired shapes. Either of the first and second positions in the defining steps may be a closed position and the other of the first and second positions may be a partially open position.

2. Second Embodiment

In one aspect, this invention is a cardiac valve prosthesis comprising a substantially cylindrical frame defining a blood flow axis, the frame having first and second ends, one of the ends defining at least two scalloped edge positions separated by at least two posts, each post having a tip; and at least two flexible leaflets attached to the frame, the at least two leaflets being configured to be movable from an open to a closed position, the at least two leaflets having a blood inlet side and a blood outlet side, the at least two leaflets being in the closed position when fluid pressure is applied to the outlet side, being in the open position when fluid pressure is applied to the inlet side and being in a neutral position intermediate the open and closed position, in the absence of fluid pressure being applied to the leaflets, each leaflet having a fixed edge joined to a respective scalloped edge portion of the frame and a free edge extending substantially between the tips of two posts. The at least two leaflets may include a first leaflet having a surface contour such that when the first leaflet is in the neutral position an intersection of the first leaflet with at least one plane perpendicular to the blood flow axis forms a first composite wave, the first composite wave being substantially defined by a first wave combined with at least a second wave superimposed over the first wave, the first wave having a first frequency, the second wave having a second frequency different than the first frequency, the first wave comprising a circular arc.

The first wave may be defined by a first wave combined with second and third waves superimposed over the first wave, the third wave having a third frequency which is different from the first and second frequencies. The first composite wave as well as the second wave may be symmetric or asymmetric about a plane parallel to and intersecting the blood flow axis and bisecting the first leaflet. The at least two leaflets may further include second and third leaflets; and an intersection of the second and third leaflets with the plane perpendicular to the blood flow axis may form second and third composite waves, respectively, the second and third composite waves being substantially the same as the first composite wave. The second wave may be defined by an equation which is one of trigonometric, elliptical, hyperbolic, a smooth analytic function and a table of values. The at least two leaflets may be configured such that they are substantially free of bending stresses when in the neutral position. The first leaflet may have a surface contour such that when the first leaflet is in the neutral position an intersection of the first leaflet with a plane parallel to and intersecting the blood flow axis and bisecting the first leaflet forms a fourth wave.

In a second aspect, this invention is a method of making a cardiac valve prosthesis which includes a substantially cylindrical frame defining a blood flow axis substantially parallel to the flow of blood through the valve prosthesis and at least two flexible leaflets attached to the frame, the method comprising forming at least two scalloped edge portions on the frame, the shape of each scalloped edge portion being defined by the intersection of the frame with a plane inclined with respect to the blood flow axis; treating the frame to raise its surface energy to above about 64 mN/m; providing a forming element having at least two leaflet forming surfaces; engaging the forming element to the frame; applying a coating over the frame and engaged forming element, the coating binding to the frame, the coating over the leaflet forming surfaces forming the at least two flexible leaflets, the at least two leaflets being configured to be movable from an open to a closed position, the at least two leaflets having a blood inlet side and a blood outlet side, the at least two leaflets being in the closed position when fluid pressure is applied to the outlet side, being in the open position when fluid pressure is applied to the inlet side and being in a neutral position intermediate the open and closed position, in the absence of fluid pressure being applied to the leaflets, the at least two leaflets including a first leaflet having a surface contour such that when the first leaflet is in the neutral position an intersection of the first leaflet with at least one plane perpendicular to the blood flow axis forms a first composite wave, the first composite wave being substantially defined by a first wave combined with at least a second superimposed wave, the first wave having a first frequency, the second wave having a second frequency, the first frequency being different from the second frequency, the first wave comprising a circular arc; and disengaging the forming element from the frame.

Figure 1:
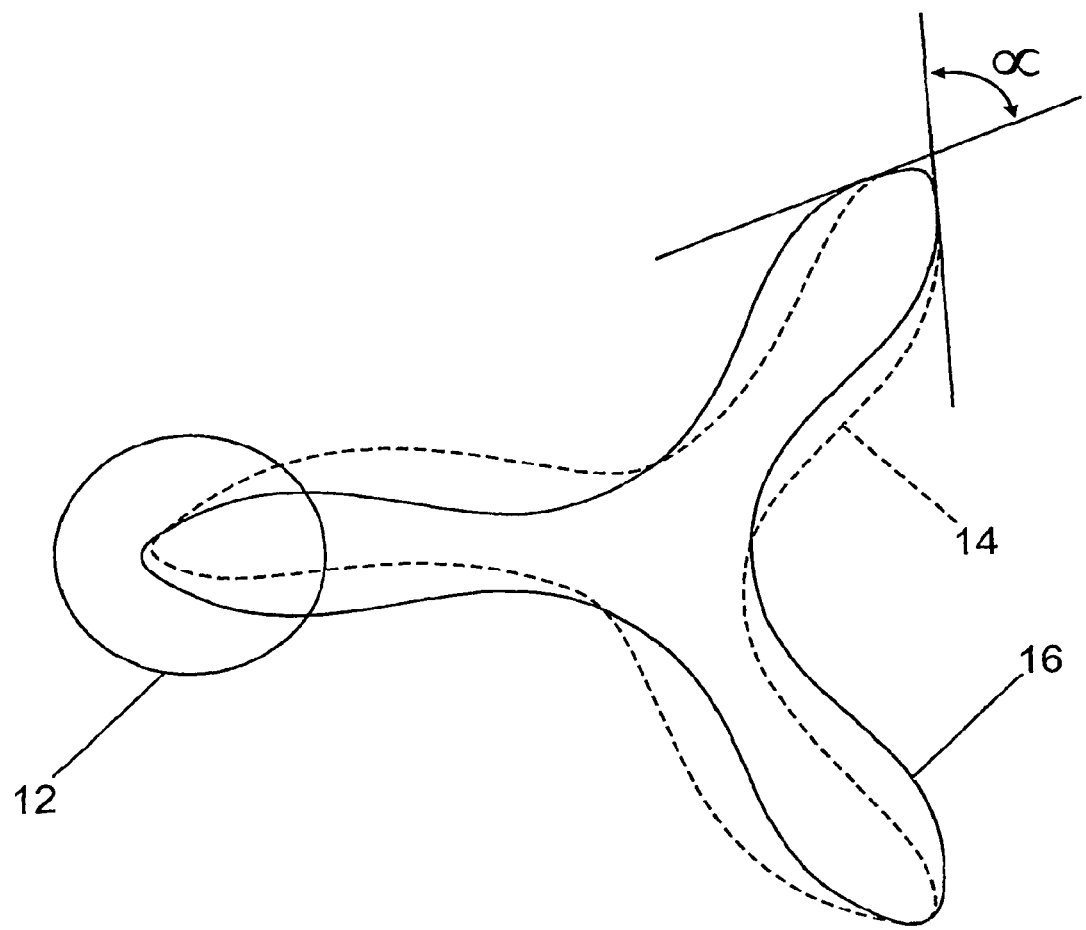
FIG. 1 is a diagrammatic view comparing the shape of symmetric (solid line) and asymmetric (dashed line) leaflets.

DESCRIPTION OF THE INVENTION a. Design Considerations

Consideration of the factors discussed above results in the identification of certain design goals which are achieved by the prosthetic heart valve of the present invention. First, the prosthetic heart valve must have enough material in the leaflet for wide opening and low closing, but more than this amount increases the energy barrier to opening. To ensure that there is sufficient, but not an excess of material, a draping analysis discussed in more detail below is used. Second, to ensure sufficient material for wide opening and low closing, the valve can only be manufactured in a partially open position: (a) by deforming the stent posts outwards during manufacture; (b) by introducing multiple curves in the leaflet free edge (but see below); (c) by making the closed position asymmetric; and (d) combinations of the above. Third, if there is enough material for low closing and wide opening, the energy barrier to opening may be high enough to prevent opening of all leaflets at low flow. The energy barrier can be minimized by: (a) introducing multiple curves in the leaflet; (b) making the leaflet asymmetric; and combinations of the above. Fourth, open commissures are needed for blood handling and closed commissures are needed for regurgitation, so the valve should have partially open commissures. In particular the included angle between adjacent leaflet free edges at the valve commissures (for example see angle α of the symmetric leaflets shown in FIG. 1) should be in the range of 10-55°, preferably in the range 25-55°.

As discussed above, the use of multiple curves in the leaflet helps assure wide opening and more complete closure of the valve and to minimize the energy barrier to opening of the valve. However, the introduction of multiple curves of more than 1.5 wavelengths to the leaflet can be a disadvantage. While there may be sufficient material in the leaflet to allow full opening, in order for this to happen, the bends in the leaflet must straighten out completely. The energy available to do this arises only from the pressure gradient across the open valve, which decreases as the leaflets becomes more open, i.e., as the valve orifice area increases. This energy is relatively small (the more successful the valve design the smaller it becomes), and does not provide enough energy to remove leaflet curves of more than 1.5 wavelengths given the stiffness of the materials available for valve manufacture. The result is they do not straighten out and the valve does not open fully.

A draping analysis is used as a first approximation to full finite element analysis to determine if the starting shape of a membrane is such that it will take on a desired final shape when placed in its final position. From a durability standpoint the focus is on the closed position, and the desired shape of the leaflet in its closed position is defined. Draping analysis allows the leaflet to be reformed in a partially open position.

Draping analysis assumes that very low energy deformation is possible (in reality any form of deformation requires energy). In order for this to occur the bending stiffness of the leaflet/membrane must be small, each element of the membrane should be free to deform relative to its neighbour, and each element should be free to change shape, i.e., the shear modulus of the material is assumed to be very low. In applying the draping analysis, it is assumed that the leaflet can be moved readily from an original defined closed position to a new position in which it is manufactured. When the valve is actually cycled, it is assumed that the leaflet when closing will move from the manufactured position to the originally defined closed position. This allows the closed position to be optimised from a stress distribution aspect, and the manufactured position to be optimised from the point of view of reducing the energy barrier to opening.

Both symmetric and asymmetric shapes of the leaflet can allow incorporation of sufficient material in the leaflet free edge to allow full opening. FIG. 1 is a diagrammatic view comparing the shape of symmetric (solid line) and asymmetric (dashed line) leaflets and also showing the commissure area 12 where the leaflets connect to the frame. An advantage of the asymmetric shape is that a region of higher radius of curvature 14 is produced than is achieved with a symmetric curve having a lower radius of curvature 16. This region can buckle more readily and thereby the energy barrier to opening is reduced.

An asymmetric leaflet also reduces the energy barrier through producing unstable buckling in the leaflet. During opening symmetric leaflets buckle symmetrically i.e., the leaflet buckles are generally mirrored about the centerline of the leaflet thus balancing the bending energies about this centerline. In the asymmetric valve the region of higher radius buckles readily, and because these bending energies are not balanced about the center line, this buckle proceeds to roll through the leaflet producing a sail-like motion producing a low energy path to open.

An additional feature of the asymmetric valve is that the open position is also slightly asymmetric, as a result of which it offers a somewhat helical flow path, and this can be matched to the natural helical sense of the aorta. Suggested benefits of this helical flow path include reduction of shear stress non-uniformity at the wall, and consequent reduction of platelet activation.

b. The Valve Prosthesis

Figure 2:
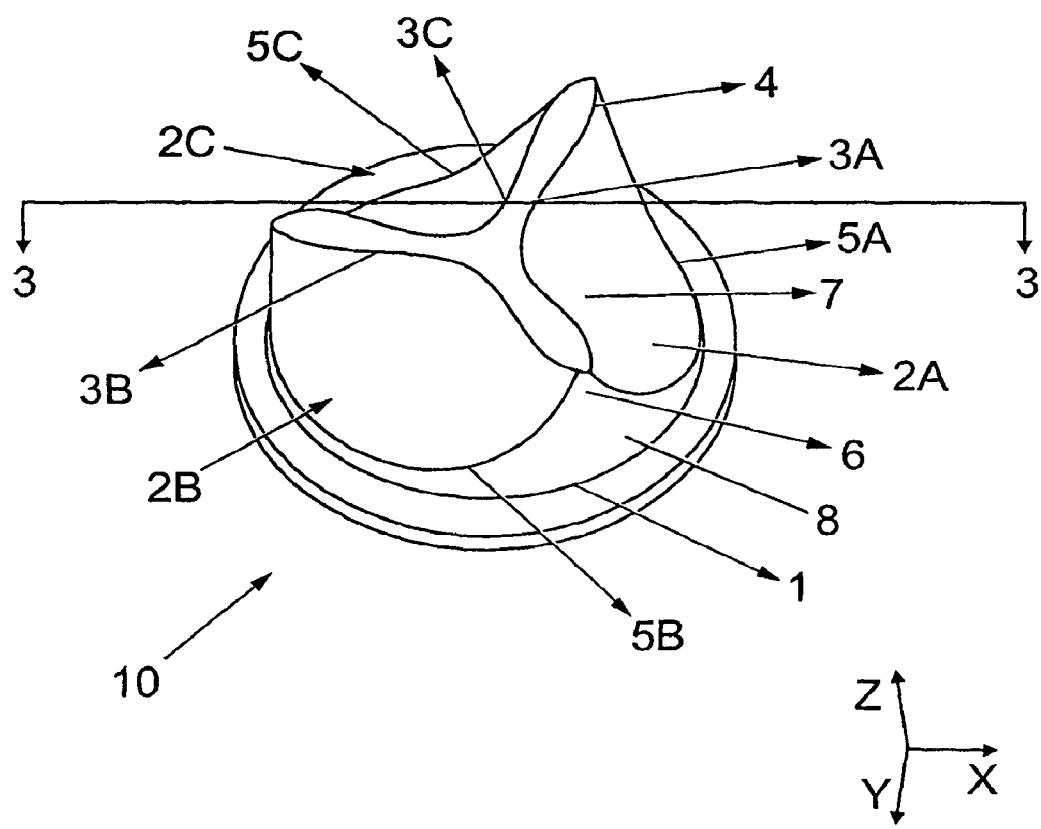
FIG. 2 is a perspective view of the valve prosthesis in the neutral or partially open position.

First and second embodiments of the valve prosthesis will be described with reference to the accompanying drawings. FIG. 2 is a perspective view of a heart valve prosthesis made in accordance with the present invention. The valve 10 comprises a stent or frame 1 and attached leaflets 2a, 2b, and 2c. The leaflets are joined to the frame at scallops 5a, 5b, and 5c. Between each scallop is post 8, the most down-stream part of which is known as a stent tip 6. Leaflets 2a, 2b, and 2c have free edges 3a, 3b, and 3c, respectively. The areas between the leaflets at the stent tips 6 form commissures 4.

1. First Embodiment of Heart Valve Prosthesis

The following describes a particular way of designing a first embodiment of a valve of the present invention. Other different design methodology could be utilized to design a valve having the structural features of the valve disclosed herein. Five computational steps are involved in this particular method:

(1) Define the scallop geometry (the scallop, 5, is the intersection of the leaflet, 2, with the frame, 1);

(2) Geometrically define a valve leaflet in the closed position C;
(3) Map and compute the distribution of area across the leaflet in the closed position;
(4) Rebuild the leaflet in a partially open position P; and
(5) Match the computed leaflet area distribution in the partially open or molded position P to the defined leaflet in the closed position C. This ensures that when an increasing closing pressure is applied to the leaflets, they eventually assume a shape which is equivalent to that defined in closed position C.

This approach allows the closed shape of the leaflets in position C to be optimised for durability while the leaflets shaped in the molded partially open shape P can be optimised for hemodynamics. This allows the use of stiffer leaflet materials for valves which have good hemodynamics. An XYZ co-ordinate system is defined as shown in FIG. 2, with the Z axis in the flow direction of blood flowing through the valve.

The leaflets are mounted on the frame, the shape of which results from the intersection of the aforementioned leaflet shape and a 3-dimensional geometry that can be cylindrical, conical or spherical in nature. A scallop shape is defined through intersecting the surface enclosed by the following equations with a cylinder of radius R (where R is the internal radius of the valve):

$$X_{eff} = E_{sO} - E_{sJ}\sqrt{1 - (Z/E_{sN})^2}$$

$$H_{sJ} = E_{sO} - E_{sJ}\sqrt{(1 - (Z/E_{sN})^2)} - H_{sO}$$

$$H_{sN}(Z) = H_{sJ} \cdot \tan(60) \cdot f(Z)$$

where $f(Z)$ is a function changing with Z.

$$X_{hyp} = H_{sO} + H_{sJ}\sqrt{(1 - (Y/H_{sN})^2)}$$

The shape of the scallop can be varied using the constants $E_{sO}$, $E_{s1}$, $H_{sO}$, $f(Z)$. The definition of parameters used in these and the other equations herein are contained in Table 4.

The shape of the leaflet under back pressure (i.e., in the closed position C) can be approximated mathematically using elliptical or hyperbolic co-ordinates, or a combination of the above in an XYZ co-ordinate system where XY is the plane of the valve perpendicular to the blood flow and Z is the direction parallel to the blood flow. The parameters are chosen to define approximately the shape of the leaflet under back pressure so as to allow convenient leaflet re-opening and minimize the effect of the stress component which acts in the direction parallel to the blood flow, whilst also producing an effective seal under back pressure.

The closed leaflet geometry in closed position C is chosen to minimize stress concentrations in the leaflet particularly prone to occur at the valve commissures. The specifications for this shape include:
(1) inclusion of sufficient material to allow a large open-leaflet orifice;
(2) arrangement of this material to minimize redundancy (excess material in the free edge, 3) and twisting in the centre of the free edge, 3; and
(3) arrangement of this material to ensure the free edge, 3, is under low stress i.e., compelling the frame and leaflet belly to sustain the back-pressure.

Figure 3:
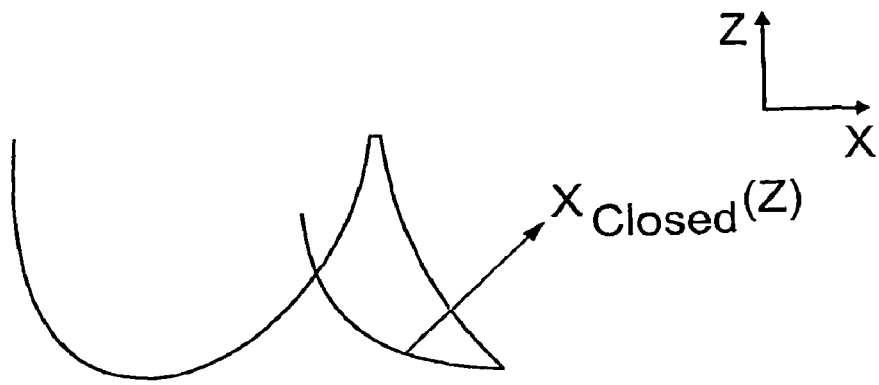
FIG. 3 is a sectional view similar to the sectional view along line 3-3 of FIG. 2 except that FIG. 3 illustrates that view when the leaflets are in the closed position and illustrates the function which is used to define the shape of the closed leaflet belly $X_{Closed}(Z)$.

FIG. 3 is a partial sectional view (using the section 3-3 shown in FIG. 2) showing only the intended position of the leaflet in the closed position. The shape of this intended position is represented by the function $X_{Closed}(Z)$. This function can be used to arrange the shape of the leaflet in the closed position C to meet the aforementioned specification. The curve is defined using the following equation and manipulated using the constants $E_{c1}$, $E_{cO}$, $Z_{cO}$ and the functions $E_{cN}(Z)$ and $X_T(Z)$.

$$X_{Closed}(Z) = -\left[E_{cJ}\left(1 - \left(\frac{Z - Z_{cO}}{E_{cN}(Z)}\right)^2\right)\right]^{0.5} + E_{cO} - X_T(Z)$$

where $E_{cN}$ is a function changing linearly with Z and $X_T(Z)$ is a function changing nonlinearly with Z.

Thus the scallop shape and the function $X_{Closed}(Z)$ are used to form the prominent boundaries for the closed leaflet in the closed position C. The remaining part of the leaflet is formed using contours $S(X, Y)_n$ sweeping from the scallop to the closed leaflet belly function $X_{closed}(Z)$, where n is an infinite number of contours, two of which are shown in FIG. 4B.

The length of the leaflet (or contours $S(X, Y)_n$) in the circumferential direction (XY) is calculated and repeated in the radial direction (Z) yielding a function L(Z) which is used later in the definition of the geometry in the partially open position P. The area contained between respective contours is also computed yielding a function K(Z) which is also used in the definition of the geometry in position P. The area contained between contours is approximated using the process of triangulation as shown in FIG. 4B. This entire process can be shortened by reducing the number of contours used to represent the surface (100<n<200).

The aforementioned processes essentially define the leaflet shape and can be manipulated to optimise for durability. In order to optimise for hemodynamics, the same leaflet is molded in a position P which is intermediate in terms of valve opening. This entails molding large radius curves into the leaflet which then serve to reduce the energy required to buckle the leaflet from the closed to the open position. The large radius curves can be arranged in many different ways. Some of these are outlined herein.

Figure 14:
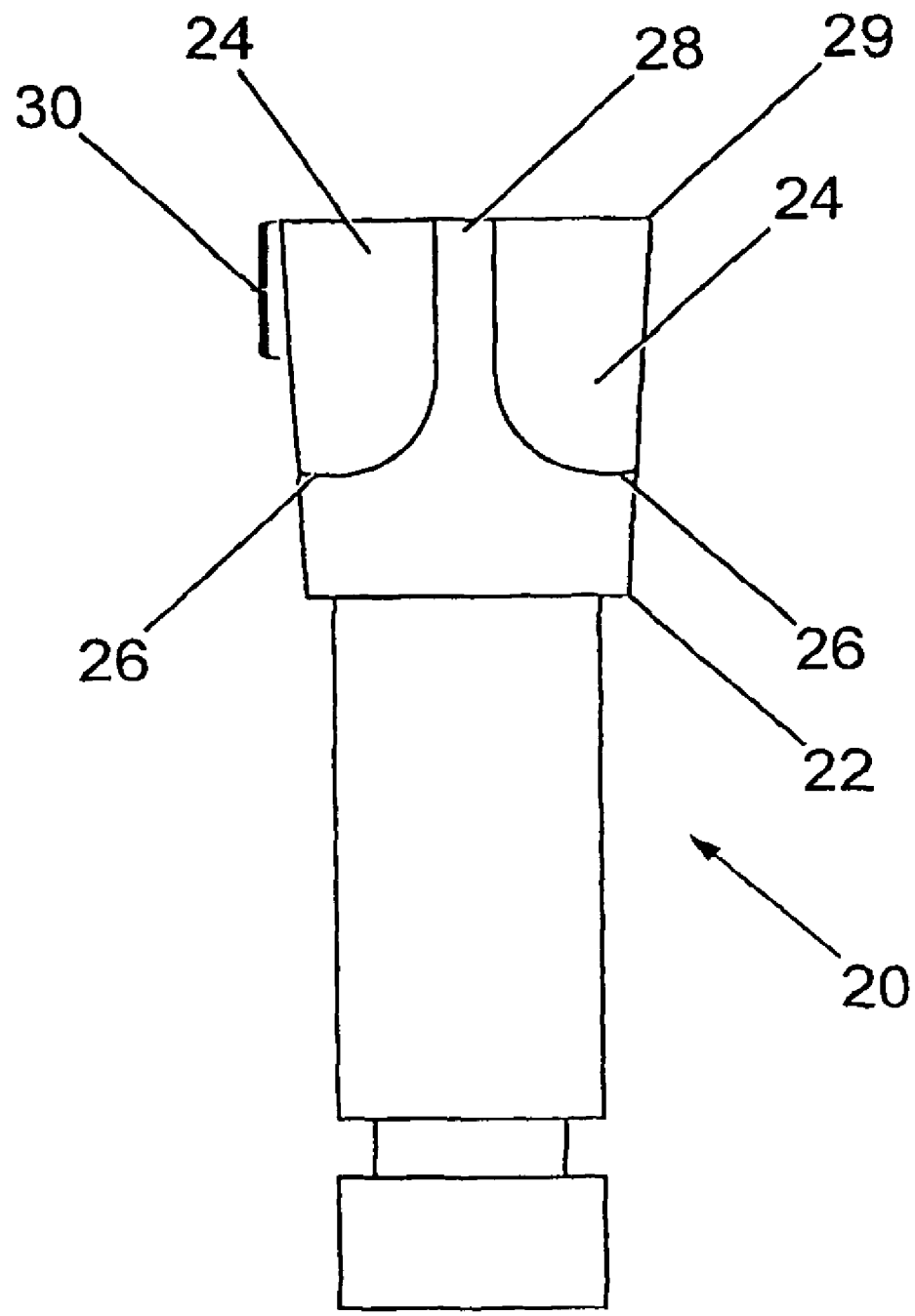
FIG. 14 is a side view of a former used in the manufacture of the valve of the present invention.

The leaflet may be molded on a dipping former as shown in FIG. 14. Preferably the former is tapered with an included angle θ so that the end 29 has a diameter which is greater than the end 22. (This ensures apposition of the frame and former during manufacture.) In this case, the scallop shape, defined earlier, is redefined to lie on a tapered geometry (as opposed to the cylindrical geometry used in the definition of the closed leaflet shape). This is achieved by moving each point on the scallop radially, and in the same movement, rotation of each point about an X-Y plane coincident with the bottom of the scallop, until each point lies on the tapered geometry.

The geometry of the leaflet shape can be defined as a trigonometric arrangement (or other mathematical function) preferably sinusoidal in nature in the XY plane, comprising one or more waves, and having anchoring points on the frame. Thus the valve leaflets are defined by combining at least two mathematical functions to produce composite waves, and by using these waves to enclose the leaflet surface with the aforementioned scallop.

One such possible manifestation is a composite curve consisting of an underlying low frequency sinusoidal wave upon which a second higher frequency sinusoidal wave is superimposed. A third wave having a frequency different from the first and second waves could also be superimposed over the resulting composite wave. This ensures a wider angle between adjacent leaflets in the region of the commissures when the valve is fully open thus ensuring good wash-out of this region.

The composite curve, and the resulting leaflet, can be either symmetric or asymmetric about a plane parallel to the blood flow direction and bisecting a line drawn between two stent tips such as, for leaflet 2a, the section along line 3-3 of FIG. 2. The asymmetry can be effected either by combining a symmetric underlying curve with an asymmetric superimposed curve or vice versa.

The following describes the use of a symmetric underlying function with an asymmetric superimposed function, but the use of an asymmetric underlying function will be obvious to one skilled in the art. The underlying function is defined in the XY plane and connects the leaflet attachment points to the scallop at a given height from the base of the valve. This underlying function shown in FIG. 5, can be trigonometric, elliptical, hyperbolic, parabolic, circular, or other smooth analytic function or could be a table of values.

Figure 5:
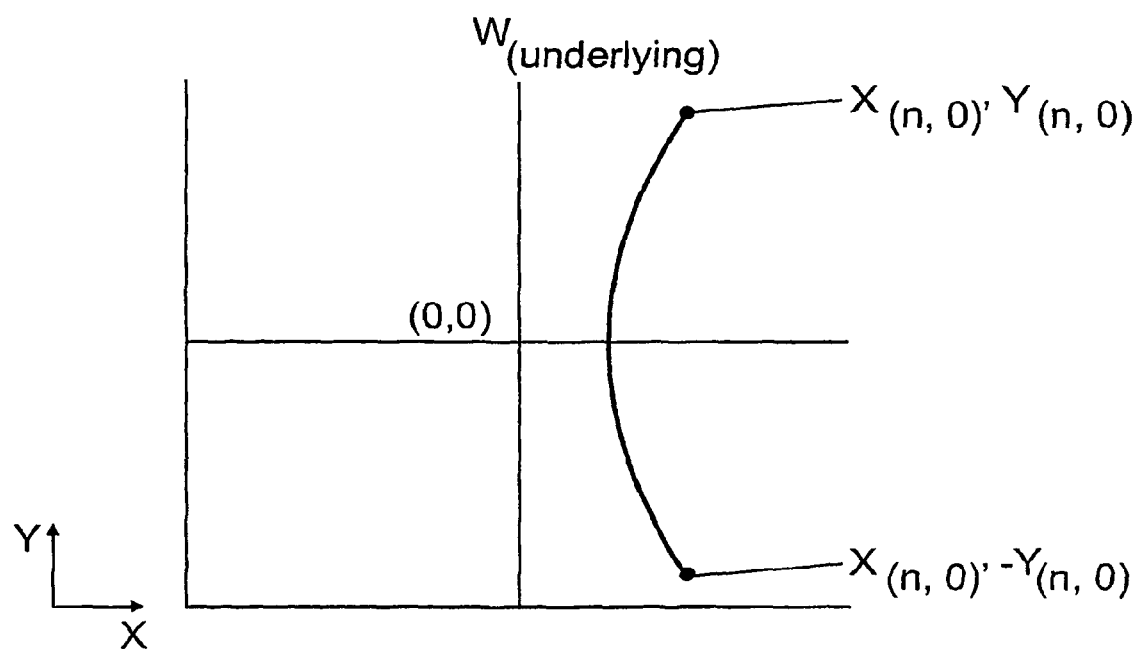
FIG. 5 is a plot of an underlying function used in defining the valve leaflet in the molded leaflet partially open position P for valves made in accordance with the first embodiment.

Using sine functions, one possible underlying wave is shown in FIG. 5 and is defined using the following equation.

$$X_u = X_{(n,0)} + A_u \cdot \sin\left[\left(\frac{0.5\pi}{Y_{(n,0)}}\right) \cdot (Y - Y_{(n,0)})\right]$$

The superimposed wave is defined in the XY plane, and connects the attachment points of the leaflet to the scallop at a given height above the base of the valve. The superimposed wave is of higher frequency than the underlying wave, and can be trigonometric, elliptic, hyperbolic, parabolic, circular, or other smooth analytic function, or a table of values.

Using sine functions, one possible symmetric leaflet design is formed when the underlying wave is combined with a superimposed wave formed using the following equation.

$$X_s = -A_s \cdot B_s(Y) \cdot \sin\left[\left(\frac{1.5 \cdot \pi}{Y_{(n,0)}}\right) \cdot (Y - Y_{(n,0)})\right]$$

Figure 6:
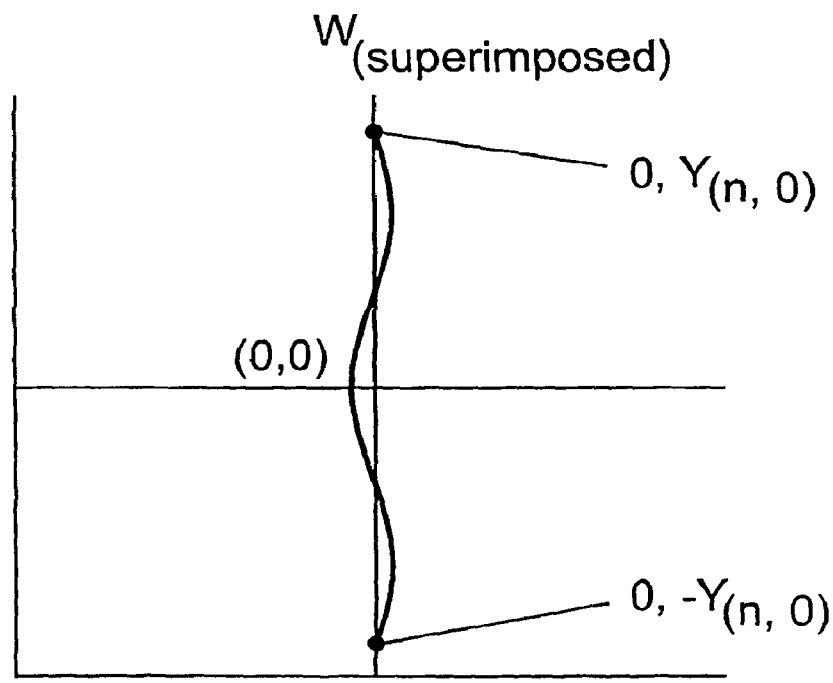
FIG. 6 is a plot of a symmetrical superimposed function used in defining the shape of the valve leaflet of the first embodiment in the molded leaflet position P.
Figure 7:
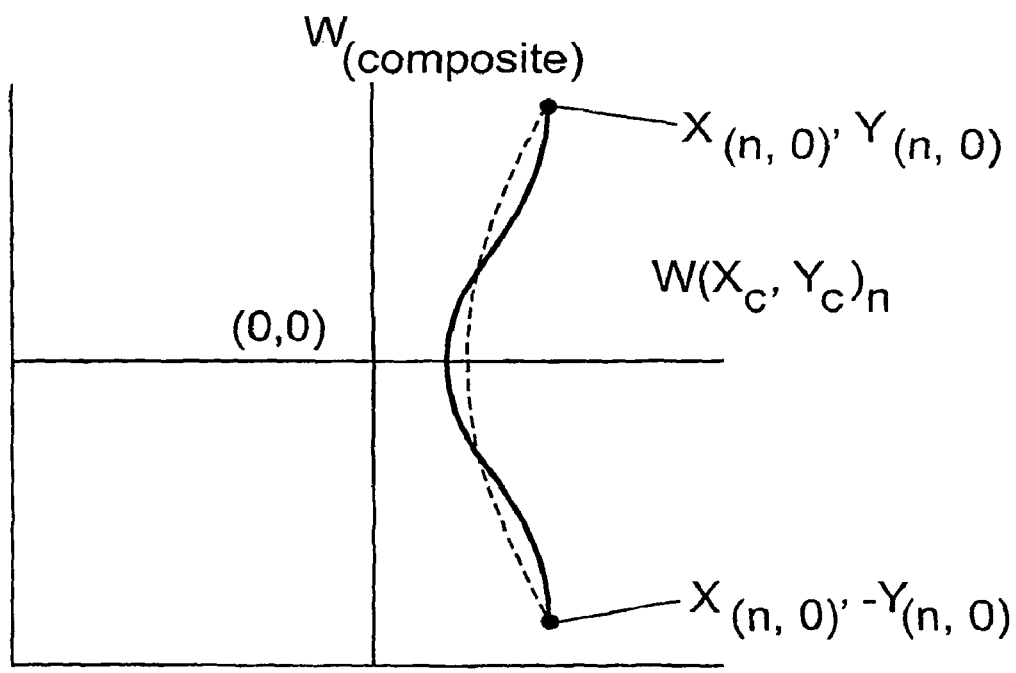
FIG. 7 is a plot of the composite function used in construction of the molded leaflet position P resulting from combining an underlying function (FIG. 5) and a symmetric superimposed function (FIG. 6) for valves made in accordance with the first embodiment.

$A_s$ can be varied across the leaflet to produce varying wave amplitude across the leaflet, for example lower amplitude at the commissures than in the leaflet centre. $B_s$ can be varied to adjust the length of the wave. The superimposed wave is shown in FIG. 6. The composite wave formed by combining the underlying wave (FIG. 5) with the superimposed wave (FIG. 6) is shown in FIG. 7.

Using sine functions, one possible asymmetric leaflet design is formed when the underlying wave (FIG. 5) is combined with a superimposed wave formed using the following equation.

$$X_s = -A_s \cdot B_s(Y) \cdot \sin\left[\left(\frac{\pi}{Y_{(n,0)}}\right) \cdot (Y - Y_{(n,0)})\right]\Big|_0^{Y_{(n,0)}}$$

$$X_s = 0.5 \cdot A_s \cdot B_s(Y) \cdot \sin\left[\left(\frac{2.0\pi}{Y_{(n,0)}}\right) \cdot Y\right]\Big|_{-Y_{(n,0)}}^0$$

Figure 8:
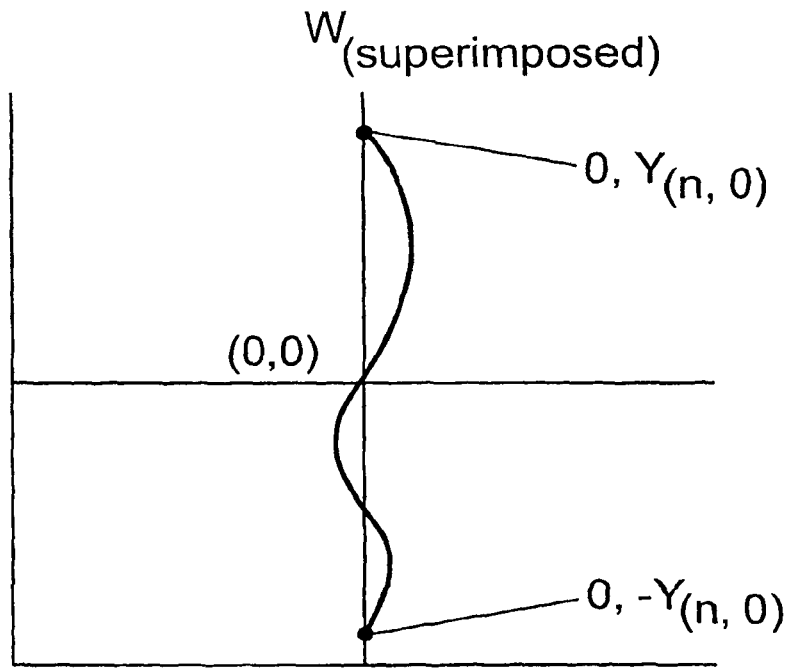
FIG. 8 is a plot of an asymmetric superimposed function used in the construction of the molded leaflet position P for valves made in accordance with the first embodiment.
Figure 9:
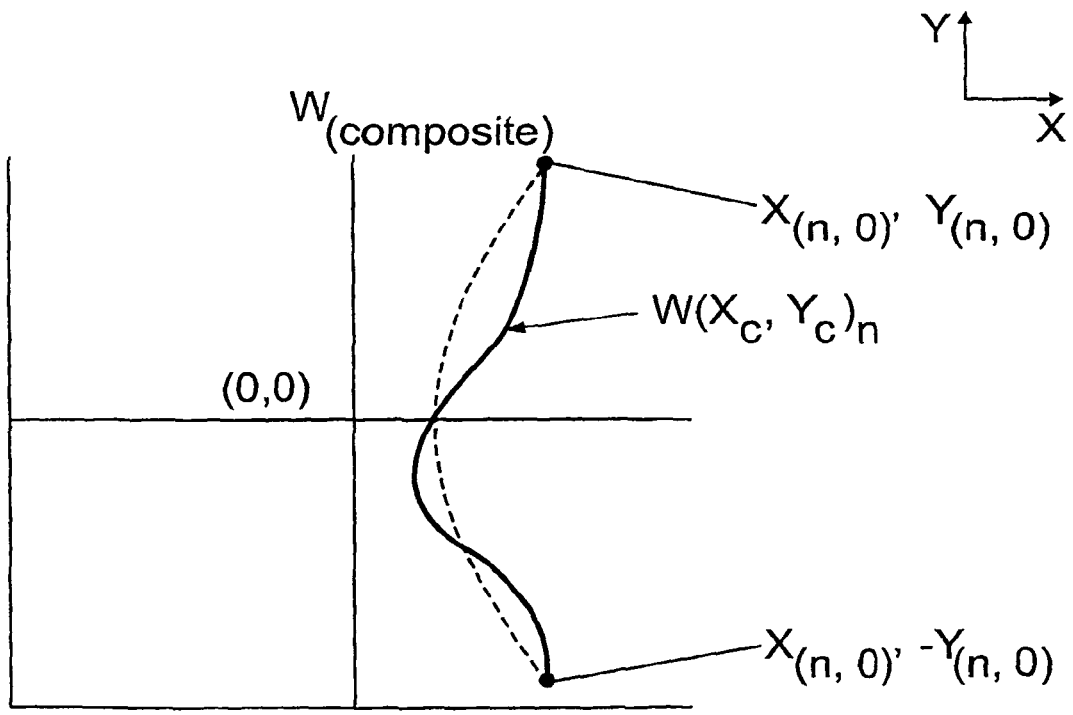
FIG. 9 is a plot of the composite function resulting from combining an underlying function (FIG. 5) and an asymmetric function (FIG. 8) for valves made in accordance with the first embodiment.

$A_s$ can be varied across the leaflet to produce varying wave amplitude across the leaflet, for example lower amplitude at the commissures than in the leaflet centre. $B_s(Y)$ can be varied to adjust the length of the wave. The superimposed wave is shown in FIG. 8. The resulting asymmetric composite wave is shown in FIG. 9. The composite wave $W(X_c, Y_c)_n$ is created by offsetting the superimposed wave normal to the surface of the underlying wave (FIGS. 7, 9).

While the general shape of the leaflet in position P has been determined using the composite wave, at this stage it is not specified in any particular position. In order to specify the position of P, the shape of the partially open leaflet position can be defined as $X_{open}(Z)$. This is shown as reference numeral 7 in FIG. 10.

One possible function determining this shape is given as follows:

$$X_{open}(Z) = -\left[E_{oJ} \cdot \left(1 - \left(\frac{Z - Z_{oO}}{E_{oN}}\right)^2\right)\right]^{0.5} + E_{oO}$$

In order to manipulate the composite wave to produce the belly shape $X_{open}(Z)$ the respective amplitudes of the individual sine waves can be varied from the free edge to the leaflet base. For example, the degree of 'openness' of the leaflet in position P can be varied throughout the leaflet.

The composite wave is thus defined to produce the molded "buckle" in the leaflet, and $X_{open}(Z)$ is used to define the geometry of the leaflet at position P. At this stage it may bear no relation to the closed leaflet shape in position C. In order to match the area distribution of both leaflet positions, (thus producing essentially the same leaflet in different positions) the composite wave length is iterated to match the length of the relevant leaflet contour in position C. Thus the amplitude and frequency of the individual waves can be varied in such a manner as to balance between: (a) producing a resultant wave the length of which is equal to the relevant value in the length function L(Z) thus approximating the required closed shape when back pressure is applied, and (b) allowing efficient orifice washout and ready leaflet opening. Also the area contained between the contours in the open leaflet is measured using the same process of triangulation as in the closed position C, and is iterated until it matches with the area contained between relevant contours in position C (denoted K(Z)) (through tilting the contours in P relative to each other). Thus the composite waves $(P(X,Y)_n)$ pertaining to the contour n and length L(Z) can be tilted at an angle to the XY plane about attachment points $X_{(n,0)}$, $Y_{(n,0)}$ and $X_{(n,0)}$, $-Y_{(n,0)}$ until the correct area is contained between $P(X,Y)_n$ and $P(X,Y)_{n-1}$ (See FIGS. 10 & 11).

This process identifies the values of $B_S$, $A_U$ and the contour tilt angle to be used in constructing the mold for the valve leaflet. As long as the constants such as $B_s$ and $A_u$, and the tilt angle of the contours relative to the XY plane, are known, the surface of the leaflet in its molded position can be visualised, enclosed and machined in a conventional manner. As a result of this fitting process the composite wave retains the same basic form but changes in detail from the top of the leaflet to the bottom of the leaflet. A composite wave can be defined in the leaflet surface as the intersection of the leaflet surface with a plane normal to the Z axis. This composite wave will have the same general form as the composite wave used in the leaflet design but will differ from it in detail as a result of the tilting process described above.

In summary therefore one possible method of designing the leaflet of the first embodiment of the present invention is in the following way:
   (1) Define a scallop shape;
   (2) Define a shape approximating the shape of the closed leaflet using elliptical, hyperbolic, parabolic or circular functions, smooth analytical functions or table of values;
   (3) Compute the functions L(Z) and K(Z), which define the length of the leaflet in the XY plane along the Z axis and the area distribution of the leaflet along the Z axis;

(4) Use one or more associated sine waves to generate a geometry which is partially-open, which pertains to a leaflet position which is between the two extreme conditions of normal valve function, i.e., leaflet open and leaflet closed;

(5) Vary the frequency and amplitude of the sinewaves to fit to the length function $L(Z)$ and the angle at which the contour is tilted to the XY plane to fit to the area function $K(Z)$; and (6) The respective amplitudes of the individual sine waves can be varied from the free edge to leaflet base, for example the degree of 'openness' of the leaflet can be varied throughout the leaflet.

Examples 1 and 2 set forth hereafter are examples of how the invention of the first embodiment can be put into practice. Using the scallop constants in Table 1, the constants required to produce an example of a symmetric leaflet valve (example 1, FIG. 12) and an example of an asymmetric leaflet valve (example 2, FIG. 13) are given in Table 2 and Table 3 respectively. These constants are used in conjunction with the aforementioned equations to define the leaflet geometry.

With one leaflet described using the aforementioned equations, the remaining two leaflets are generated by rotating the geometry about the Z axis through 120° and then through 240°. These leaflet shapes are inserted as the leaflet forming surfaces of the dipping mold (otherwise known as a dipping former), which then forms a 3-dimensional dipping mold. The composite wave described in the aforementioned equations, therefore substantially defines the former surface which produces the inner leaflet surface.

As seen in FIG. 14 the dipping mold 20 is slightly tapered so that the end 29 has a diameter which is greater than the end 22, and has a first end 22 having an outside diameter slightly smaller than the inside diameter of the frame. The former includes at least two and preferably three leaflet forming surfaces 24 which are defined by scalloped edges 26 and flats 28. Sharp edges in the manufacturing former and on the frame are radiused to help reduce stress concentrations in the finished valve. During the dip molding process the frame is inserted over end 22 of the former so that the scallops 5 and stent posts 8 of the frame align with the scalloped edges 26 and flats 28 of the former. The leaflet forming surfaces 24 are configured to form leaflets during the molding process which have the geometry described herein. This mold can be manufactured by various methods, such as, machining, electrical discharge machining, injection molding. In order that blood flow is not disturbed, a high surface finish on the dipping mold is essential.

For the frame there are preferably three posts with leaflets hung on the frame between the posts. A crown-like frame or stent, 1, is manufactured with a scallop geometry, which matches the dipping mold scallop. The frame scallop is offset radially by 0.1 mm to allow for the entire frame to be coated with a thin layer of leaflet material to aid adhesion of the leaflets. Leaflets may be added to the frame by a dip-molding process, using a dipping former machined or molded to create the multiple sinewave form.

The material of preference should be a semi-rigid fatigue- and creep-resistant frame material such as polyetheretherketone (PEEK), high modulus polyurethane, titanium, reinforced polyurethane, or polyacetal (Delrin) produced by machining or injection-molding etc. Alternatively, a relatively low modulus polymer may be used, which may be fibre-reinforced, to more closely mimic the aortic wall. The frame can be machined or injection molded, and is manufactured preferably from PEEK or polyacetal (Delrin).

The frame is treated by exposure to a gas plasma or other methods to raise its surface energy above 64 mN/m (milliNewtons/meter). Then the frame is dipped in a polyurethane solution (preferably Elast-Eon™ manufactured by Aortech Biomaterials Pty, Sydney Australia) in order to apply a coating of approximately 0.1 mm thick. Having dried the frame with applied coating in an oven overnight, it is placed on the dipping former and aligned with the former scallops. The combination of frame and three dimensional dipping mold is then dipped into polyurethane solution, which forms a coating of solution on frame and mold. This coating flows slowly over the entire mold surface ensuring a smooth coating. The new coating on the frame and dipping mold solvates the initial frame coating thus ensuring a good bond between leaflet and frame. The dipping mold with polyurethane covering is dried in an oven until all the solvent has been removed. One or more dips may be used to achieve a leaflet with a mean thickness between 40 µm and 500 µm. The shape of the former, and the viscosity and solvent interactive properties of the polyurethane solution, control the leaflet thickness and the distribution of thickness over the leaflet. A dipping process does not allow precise control of leaflet thickness and its variation across a leaflet. In particular, surfaces that are convex on the dipping former result in reduced leaflet thickness when compared with surfaces that are concave. Additionally the region of the leaflet adjacent to the frame essentially provides a very small concave radius which traps further polymer solution and this results in thickening of these regions.

The shape of the former is substantially defined by the composite wave. Radiusing and polishing of the former can both contribute to some variation of the shape. The shape of the inner surface of the leaflets will closely replicate the shape of the former. The shape of the outer surface of the leaflets will be similar to the shape of the inner surface but variations will result from the processing properties of the polymer solution and details of the dipping process used to produce the valve. The leaflet may be formed from polyurethanes having a Young's modulus less than 100 MPa, preferably in the range 5 to 50 MPa.

The valve is next removed from the dipping mold. The stent posts, which had been deflected by the taper on the former, now recover their original position. The shape of the leaflets changes slightly as a result of the movement of the stent posts.

At this stage the dipping mold and frame is covered with an excess of polyurethane due to the drain-off of the polymer onto the region of the mold known as the drain-off area 30. Leaflet free edges may be trimmed of excess material using a sharp blade rotated around the opened leaflets or using laser-cutting technology.

An alternate valve manufacturing method is injection molding. A mold is constructed with a cavity which allows the valve frame to be inserted in the mold. The cavity is also designed with the leaflet geometry, as defined above, as the inner leaflet surface. A desired thickness distribution is defined for the leaflet and the outer leaflet surface of the mold is constructed by adding the leaflet thickness normally to the inner leaflet surface. The leaflet may be of uniform thickness throughout, in the range 40 to 500 microns, preferably 50 to 200 microns, more preferably 80 to 150 microns. The leaflet may be thickened towards its attachment to the frame. Alternatively the thickness of the leaflet, along a cross-section defined by the intersection of a plane perpendicular to the blood flow axis and the leaflet, can change gradually and substantially continuously from a first end of the cross-section (i.e., first edge of the leaflet) to a second end of the cross-section (i.e., second edge of the leaflet) in such a way that the mean thickness of the first half of the leaflet is different from the mean thickness of the second half of the leaflet. This mold is inserted in a conventional injection molding machine, the frame is inserted in the mold and the machine injects molten polymer into the cavity to form the leaflets and bond them to the frame. The polymer solidifies on cooling and the mold is opened to allow the complete valve to be removed.

The leaflets may also be formed using a reaction-molding process (RIM) whereby the polymer is synthesized during the leaflet forming. A mold is constructed as described above. This mold is inserted in a reaction-injection molding machine, the frame is inserted in the mold and the machine injects a reactive mixture into the cavity. The polymer is produced by the reaction in the cavity to form the leaflets and bond them to the frame. When the reaction is complete, the mold is opened to allow the complete valve to be removed.

Yet a further option is to compression mold a valve initially dipped. This approach allows the leaflet thickness or thickness distribution to be adjusted from that initially produced. By varying the thickness of the leaflets the dynamics of the valve opening and closing can be modified. For example, the thickness of the leaflet along a cross-section defined by the intersection of a plane perpendicular to the blood flow axis and the leaflet can be varied so that the thickness changes gradually and substantially continuously from a first end of the cross-section (i.e., first edge of the leaflet) to a second end of the cross-section (i.e., second edge of the leaflet) in such a way that the mean thickness of the first half of the leaflet is different from the mean thickness of the second half of the leaflet. This will result in the thinner half of the leaflet opening first and creating a sail-like opening motion along the free edge of the leaflet.

Leaflet shape resulting from conventional injection molding, reaction injection molding or compression molding, is substantially defined by the composite wave described above. It will differ in detail for many of the same reasons identified for dip molding.

The valves of the present invention are manufactured in the neutral position or close to it and are therefore substantially free of bending stresses in this position. As a result when the leaflet is moved to its closed position the total bending energy at the leaflet center free edge and at the commissures is reduced compared to a valve made according to U.S. Pat. No. 5,376,113 (Jansen et al.).

The valves of the present invention may be used in any required position within the heart to control blood flow in one direction, or to control flow within any type of cardiac assist device.

The following examples 1 and 2 use the same scallop geometry described using the constants set forth in Table 1: While the examples described herein relate to one valve size, the same method can be used to produce valves from a wide range of sizes. This can be carried out by modifying the constants used in the equations, by rescaling the bounding curves such as $X_{closed}(Z)$ and computing and iterating in the normal fashion or by rescaling the leaflet.

TABLE 1

|  | values (mm) |
| --- | --- |
| R | 11.0 |
| $E_{So}$ | 21.7 |
| $E_{sJ}$ | 21.5 |
| $E_{sN}$ | 13.8 |
| $H_{sO}$ | 0.18 |
| f(Z) | (0.05.Z) + 1.0 |

EXAMPLE 1

The parameters described in the preceding sections are assigned the values set forth in Table 2 and are used to manufacture a symmetric valve. The included angle between adjacent leaflet free edges at the valve commissure for this valve is approximately 50°.

TABLE 2

| Parameter | Value (mm) |
| --- | --- |
| Closed position | |
| $Z_{cO}$ | 0 |
| $Z_{cO}$ | 0.0 |
| $E_{cN}(Z)$ | $E_{cN} = 3.0.Z + 50.3$ |
| $E_{cO}$ | 22.0 |
| $E_{cJ}$ | 20.0 |
| $X_{T(Z)}$ | 0.0 |
| Partially-open position | |
| θ | 12.7° |
| $E_{oJ}$ | 50.0 |
| $Z_{oO}$ | 4.0 |
| $E_{oO}$ | 51.8 |
| $E_{oN}$ | 27.7 |
| $A_u$ | Result from iteration procedure finds that $A_u$ varies from 1e−5 at the leaflet base to 5.1 at 4 mm from the leaflet base to 3.8 at the free edge. |
| $A_s(Y)$ | 1.0 |
| $B_s$ | Result from iteration procedure finds that $B_s$ varies from 1e−3 at the leaflet base to 1.6 at 3 mm from the leaflet base to 0.6 at the free edge. |

Figure 12:
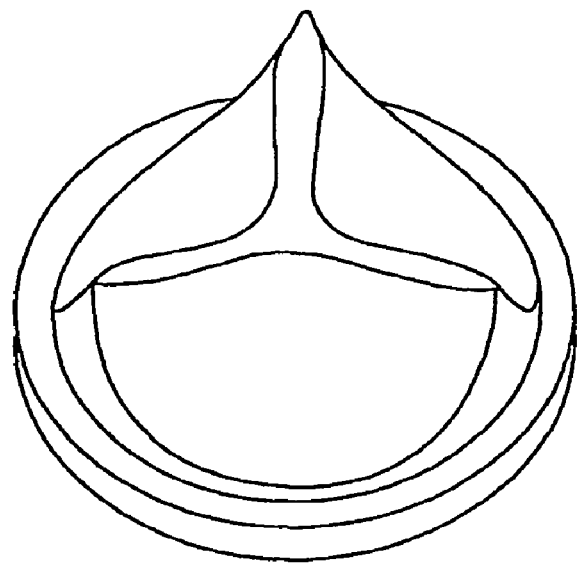
FIG. 12 is a perspective view of a valve of the first embodiment having symmetric leaflets.

FIG. 12 shows the symmetric valve which is manufactured, using the values outlined in Table 1 and Table 2.

EXAMPLE 2

The parameters described in the preceding sections are assigned the values set forth in Table 3 and are used to manufacture an asymmetric valve. The included angle between adjacent leaflet free edges at the valve commissure for this valve is approximately 48°.

TABLE 3

| Parameter | Value (mm) |
| --- | --- |
| Closed position | |
| $Z_{cO}$ | 0.0 |
| $E_{cN}(Z)$ | $E_{cN} = 3.0.Z + 48.9$ |
| $E_{cO}$ | 18.4 |
| $E_{cJ}$ | 20.0 |
| $X_{T(Z)}$ | $X_{T(n-1)} = 0.97.(X_{T(n)})$ where $X_{T(free\ edge)} = 2.1$ |
| Partially-open position | |
| θ | 7.1° |
| $E_{oJ}$ | 50.0 |
| $Z_{oO}$ | 5.0 |
| $E_{oO}$ | 51.5 |
| $E_{oN}$ | 29.0 |
| $A_u$ | Result from iteration procedure finds that $A_u$ varies from 1e−5 at the leaflet base to 3.1 at 3 mm from the leaflet base to 2.2 at 9 mm from the leaflet base to 3.8 at the free edge. |
| $A_s(Y)$ | $B_s(Y) = (Y - c)/m$ where $B_s = 1$ at leaflet base and m = 5.04 and c = −15.1 at leaflet free edge. |

TABLE 3-continued

| Parameter | Value (mm) |
|---|---|
| $B_s$ | Result from iteration procedure finds that $B_s$ varies from 1e−3 at the leaflet base to 1.1 at 6 mm from the leaflet base to 0.4 at the free edge. |

Figure 13:
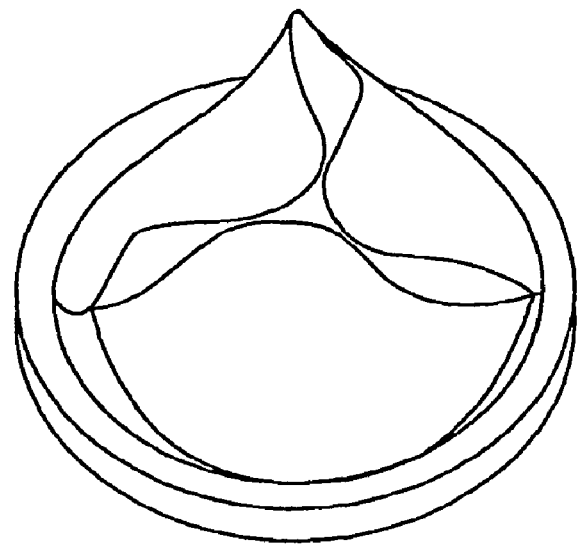
FIG. 13 is a perspective view of a valve of the first embodiment having asymmetric leaflets.

FIG. 13 shows the valve which is manufactured using the values outlined in Table 1 and Table 3.

TABLE 4

Definition of parameters

| | |
|---|---|
| R | Internal radius of valve Scallop (FIG. 2) |

$X_{ell}$, $H_{sJ}$, $H_{sN}$, $X_{hyp}$ are used to define a surface which, when intersected with a cylinder, scribe a function which forms the scallop for one leaflet. This method for creating a scallop is described in Mackay et al., Biomaterials 17 1996, although an added variable f(Z) is used for added versatility.

| | |
|---|---|
| $X_{ell}$ | Scribes an ellipse in the radial direction. |
| $X_{hyp}$ | Scribes a hyperbola in the circumferential direction. |
| $E_{sO}$ | Ellipse X-axis offset |
| $E_{sJ}$ | Major axis of the ellipse |
| $E_{sN}$ | Minor axis of the ellipse |
| $H_{sJ}$ | Major axis of the hyperbola |
| $H_{sN}$ | Minor axis of the hyperbola |
| $H_{sO}$ | Hyperbola x-axis offset |
| f(Z) | Creates a varying relationship between $H_{sN}$ and $H_{sJ}$ |

Figure 4A:
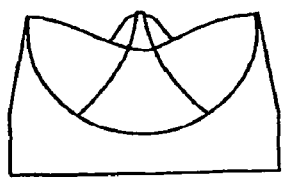
FIG. 4A is a front view of the valve leaflet shown in FIG. 2.
Figure 4B:
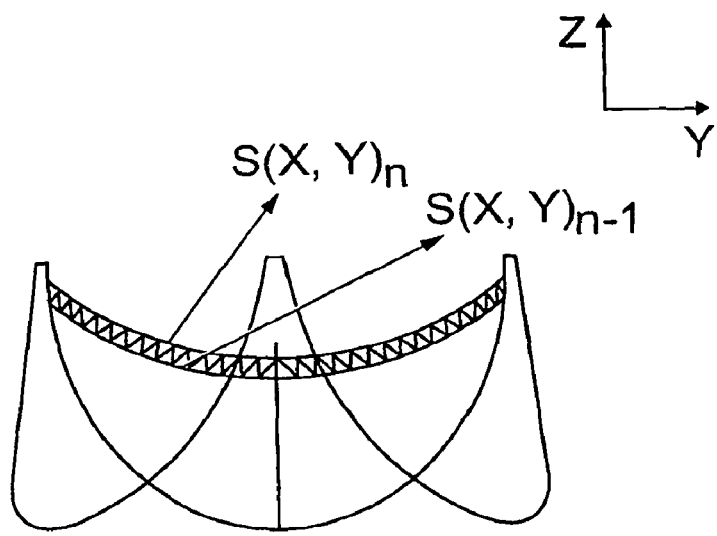
FIG. 4B is in the same view as FIG. 4A and is a partial schematic view of the same closed valve leaflet shown in FIG. 3 and illustrates that $S(X, Y)_n$ and $S(X, Y)_{n-1}$ are contours enclosing the leaflet between the function $X_{Closed}(Z)$ and the scallop geometry.

Closed Leaflet geometry C (FIGS. 3 & 4)

$X_{closed}(Z)$ is defined as an ellipse (with a minor axis $E_{cN}(Z)$ which changes with Z) in the XZ axis in the plane defined in FIG. 2 by cutting plane 3-3. It is defined using the following constants and functions.

| | |
|---|---|
| $Z_{cO}$ | Closed ellipse Z-axis offset |
| $E_{cN}(Z)$ | Closed ellipse minor axis which changes with Z |
| $E_{cO}$ | Closed ellipse X-axis offset |
| $E_{cJ}$ | Closed ellipse major axis |
| $X_{T(Z)}$ | Offset function which serves to increase the amount of material in the belly |

Molded position P

P is enclosed by a number (n) of contours $P(X,Y)_n$ which run from one side of the scallop to the other. The underlying function $X_u$ is used in defining both symmetric and asymmetric leaflets. $X_u$ is simply an ellipse (or other such function) running in a plane from one side of the scallop to the other. The points on the scallop are designated $X_{(n,0)}$, $Y_{(n,0)}$ where n refers to the contour number (see FIGS. 5, 7, 9, 11B).

| | |
|---|---|
| Y | Variable in plane from $Y_{(n,0)}$ to − $Y_{(n,0)}$ |
| $A_u$ | $A_u$ is the amplitude of the underlying wave |
| $A_s(Y)$ | $A_s$ is a function which biases the wave amplitude in a defined way, e.g. the amplitude of the wave can be increased near the commissure if so desired. |
| $B_s$ | $B_s$ is the amplitude of the superimposed wave |

Composite Curve (FIGS. 7 & 9)

| | |
|---|---|
| $X_c$ | X coordinate for defining the composite curve. This is derived using $X_u$ and $X_s$ |
| $Y_c$ | Y coordinate for defining the composite curve. This is derived using $X_u$ and $X_s$ |

TABLE 4-continued

Definition of parameters

Figure 10:
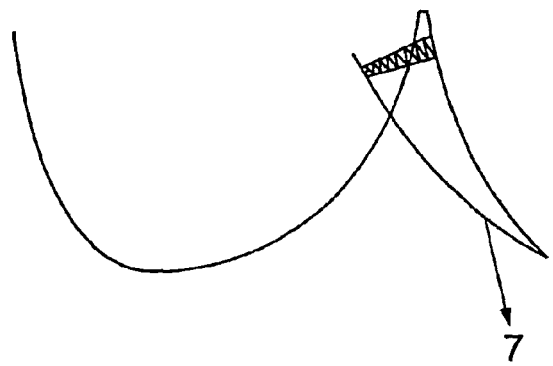
FIG. 10 is a sectional view of the valve leaflets in the neutral position along line 3-3 in FIG. 2 and illustrates the function which is used to define the shape of the molded leaflet belly $X_{open}(Z)$.
Figure 11A:
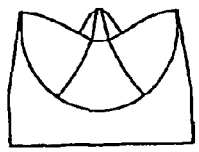
FIG. 11A is a front view of the valve.
Figure 11B:
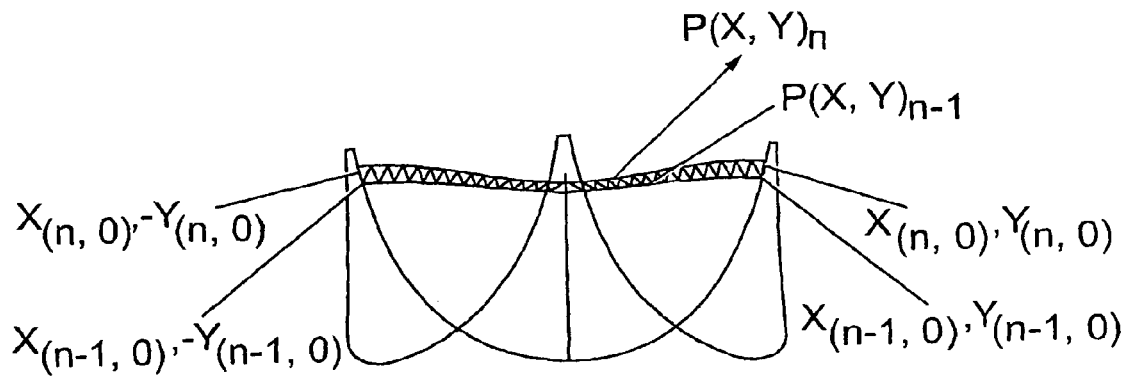
FIG. 11B is a partial schematic view of the valve leaflets of FIG. 11A and illustrates that $P(X, Y)_n$ and $P(X, Y)_{n-1}$ are contours enclosing the leaflet between the function $X_{open}(Z)$ and the scallop geometry.

Open Leaflet position (FIG. 10)

$X_{open}(Z)$ is defined as an ellipse in the XZ axis in the plane defined in FIG. 2 by cutting plane 3-3. The contours defined in Composite Curve are married to the Open Leaflet position $X_{open}(Z)$ to produce the molded leaflet P. It is defined using the following constants.

| | |
|---|---|
| $E_{oJ}$ | Open ellipse major axis |
| $Z_{oO}$ | Open ellipse Z-axis offset |
| $E_{oO}$ | Open ellipse X-axis offset |
| $E_{oN}$ | Open ellipse minor axis |
| θ | Former taper angle |

2. Second Embodiment of Heart Valve Prosthesis

The following describes another particular way of designing a second embodiment of a valve of the present invention. Other different design methodology could be utilized to design a valve having the structural features of the valve disclosed herein. Five computational steps are involved in this particular method:

(1) Define the scallop geometry (the scallop, 5, is the intersection of the leaflet, 2, with the frame, 1);

(2) Define a contour length function L(z) and use this function to define a valve leaflet in the closed position C and optimize the stress distribution on the valve. The stress distribution can be confirmed using Finite Element Analysis (FEA). Thus the resulting stress distribution results from the length function L(Z) and FEA is used to confirm the optimal L(Z);

(3) Rebuild the leaflet in a partially open position P; and (4) Match, using contour lengths, the computed leaflet area distribution in the partially open or molded position P to the defined leaflet in the closed position C. This ensures that when an increasing closing pressure is applied to the leaflets, they eventually assume a shape which is equivalent to that defined in closed position C.

This approach allows the closed shape of the leaflets in position C to be optimised for durability while the leaflets shaped in the molded partially open shape P can be optimised for hemodynamics. This allows the use of stiffer leaflet materials for valves which have good hemodynamics. An XYZ co-ordinate system is defined as shown in FIG. 2, with the Z axis in the flow direction of blood flowing through the valve.

The leaflets are mounted on the frame, the shape of which results from the intersection of the aforementioned leaflet shape and a 3-dimensional geometry that can be cylindrical, conical or spherical in nature.

The leaflets are mounted on the frame, the shape of which results from the intersection of the aforementioned leaflet shape and a 3-dimensional geometry that can be cylindrical, conical or spherical in nature. A scallop shape is defined through cutting a cylinder of radius R (where R is the internal radius of the valve) with a plane at an inclined angle. The angle of the cutting plane is dictated by the desired height of the leaflet and the desired distance between the leaflets at the commissures.

The closed leaflet geometry in closed position C is chosen to minimize stress concentrations in the leaflet particularly prone to occur at the valve commissures. The specifications for this shape include:

(1) inclusion of sufficient material to allow a large open-leaflet orifice;

(2) arrangement of this material to minimize redundancy (excess material in the free edge, 3) and twisting in the centre of the free edge, 3; and (3) arrangement of this material to ensure the free edge, 3, is under low stress i.e., compelling the frame and leaflet belly to sustain the back-pressure.

The closed leaflet geometry is formed using contours $S(X, Y)_n$ sweeping from attachment points on one side of the scallop to the congruent attachment point on the opposite side of the scallop, where n is an infinite number of contours, two of which are shown in FIG. 4B. The geometry of the contours $S(X, Y)_n$ can be simple circular arcs or a collection of circular arcs and tangential lines; the length of each contour is defined by $L(Z)$. Hence the geometry is defined and modified using the length function $L(Z)$.

Thus the scallop shape and the contours $S(X, Y)_n$ are used to form the prominent boundaries for the closed leaflet in the closed position C. This process can be shortened by reducing the number of contours used to represent the surface ($5<n<200$). For design iteration, the ease with which the leaflet shape can be changed can be improved by reducing the number of contours to a minimum (i.e., n=5), although the smoothness of the resulting leaflet could be compromised to some extent. Upon optimising the function $L(Z)$ for stress distribution, the number of contours defining the leaflet can be increased to improve the smoothness of the resulting leaflet ($100<n<200$). The function $L(Z)$ is used later in the definition of the geometry in the partially open position P.

The aforementioned processes essentially define the leaflet shape and can be manipulated to optimise for durability. In order to optimise for hemodynamics, the same leaflet is molded in a position P which is intermediate in terms of valve opening. This entails molding large radius curves into the leaflet which then serve to reduce the energy required to buckle the leaflet from the closed to the open position. The large radius curves can be arranged in many different ways. Some of these are outlined herein.

As previously described with respect to the first embodiment the leaflet may be molded on a dipping former as shown in FIG. 14. However, in this embodiment to aid removal of the valve from the former and reduce manufacturing stresses in the leaflet the former is preferably not tapered.

The geometry of the leaflet shape can be defined as a circular and trigonometric arrangement (or other mathematical function) preferably circular and sinusoidal in nature in the XY plane, comprising one or more waves, and having anchoring points on the frame. Thus the valve leaflets are defined by combining at least two mathematical functions to produce composite waves, and by using these waves to enclose the leaflet surface with the aforementioned scallop.

One such possible manifestation is a composite curve consisting of an underlying circular arc or wave upon which a second higher frequency sinusoidal wave is superimposed. A third wave having a frequency different from the first and second waves could also be superimposed over the resulting composite wave. This ensures a wider angle between adjacent leaflets in the region of the commissures when the valve is fully open thus ensuring good wash-out of this region.

The composite curve, and the resulting leaflet, can be either symmetric or asymmetric about a plane parallel to the blood flow direction and bisecting a line drawn between two stent tips such as, for leaflet 2a, the section along line 3-3 of FIG. 2. The asymmetry can be effected either by combining a symmetric underlying curve with an asymmetric superimposed curve or vice versa, or by utilising a changing wave amplitude across the leaflet.

The following describes the use of a symmetric underlying function with an asymmetric superimposed function, but the use of an asymmetric underlying function will be obvious to one skilled in the art. The underlying function is defined in the XY plane and connects the leaflet attachment points to the scallop at a given height from the base of the valve. This underlying function shown in FIG. 15, can be trigonometric, elliptical, hyperbolic, parabolic, circular, or other smooth analytic function or could be a table of values.

The superimposed wave is defined in the XY plane, and connects the attachment points of the leaflet to the scallop at a given height above the base of the valve. The superimposed wave is of higher frequency than the underlying wave, and can be trigonometric, elliptic, hyperbolic, parabolic, circular, or other smooth analytic function, or a table of values.

One possible asymmetric leaflet design is formed when the underlying wave formed using a circular arc is combined with a superimposed wave formed using the following equation.

$$X_s = A_s \cdot B_s(Y) \cdot \sin\left[\left(\frac{1.5\pi}{Y_{(n,0)}}\right) \cdot (Y - Y_{(n,0)})\right]$$

Figure 15:
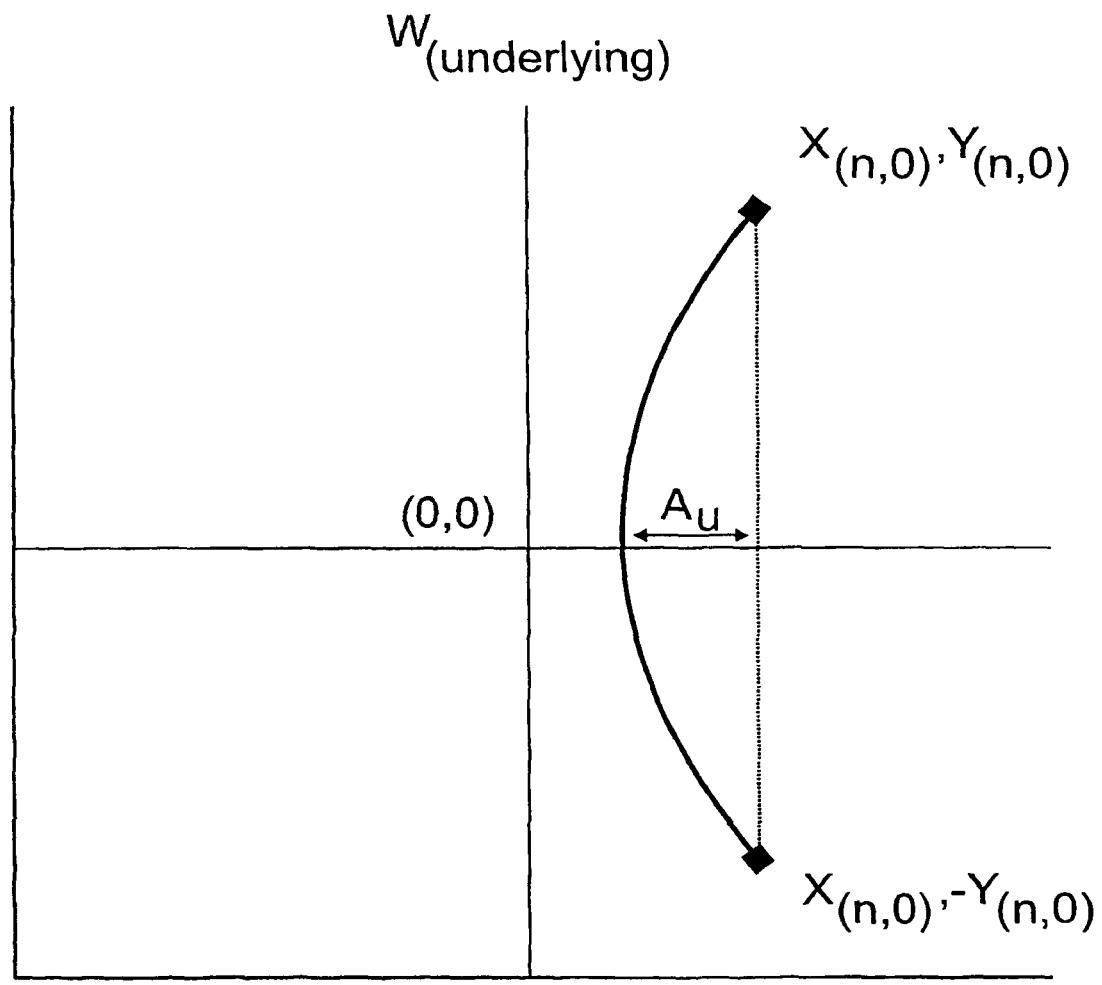
FIG. 15 is a plot of an underlying function used in defining the valve leaflet in the molded partially open position P for a valve made in accordance with the second embodiment.
Figure 16:
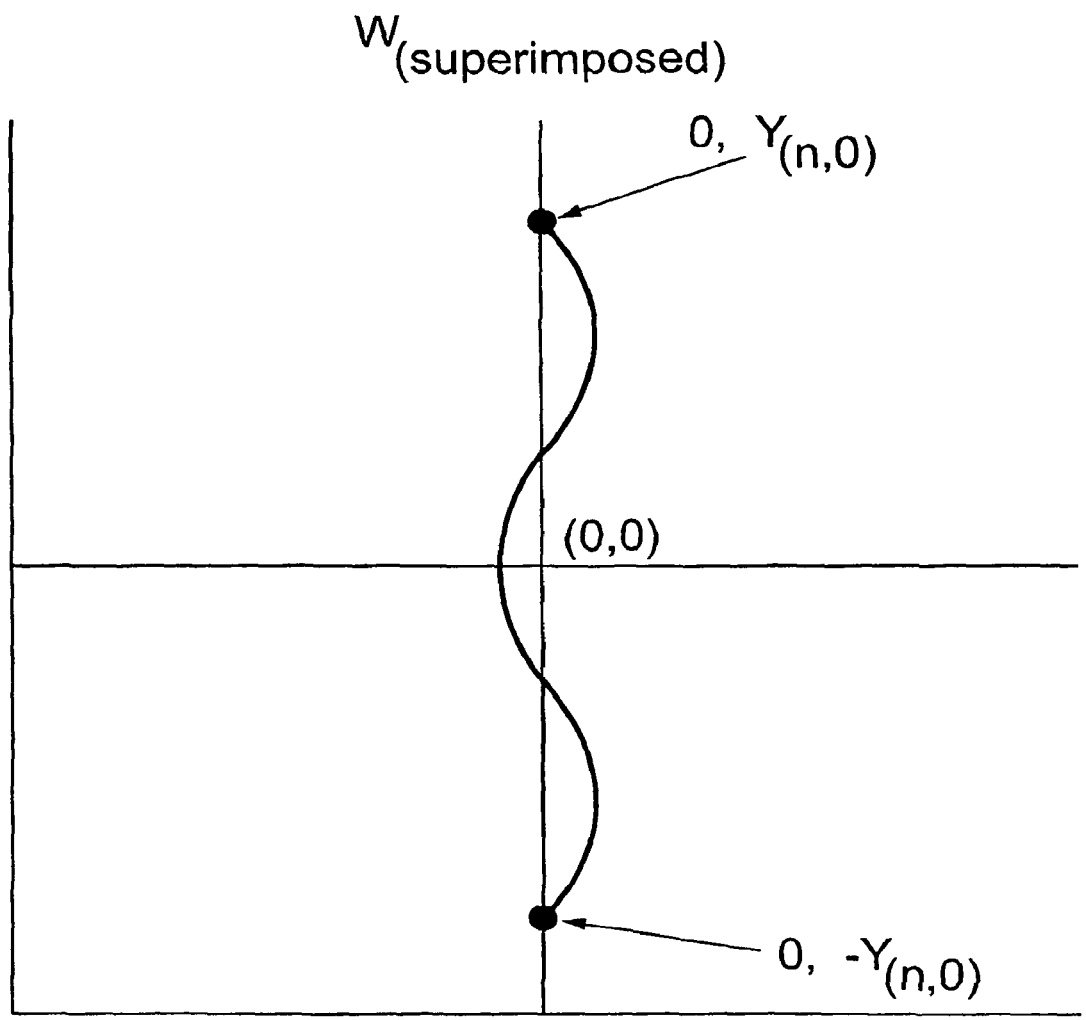
FIG. 16 is a plot of an asymmetrical superimposed function used in defining the shape of a valve leaflet of the second embodiment in the molded leaflet position P for valves made in accordance with the second embodiment.
Figure 17:
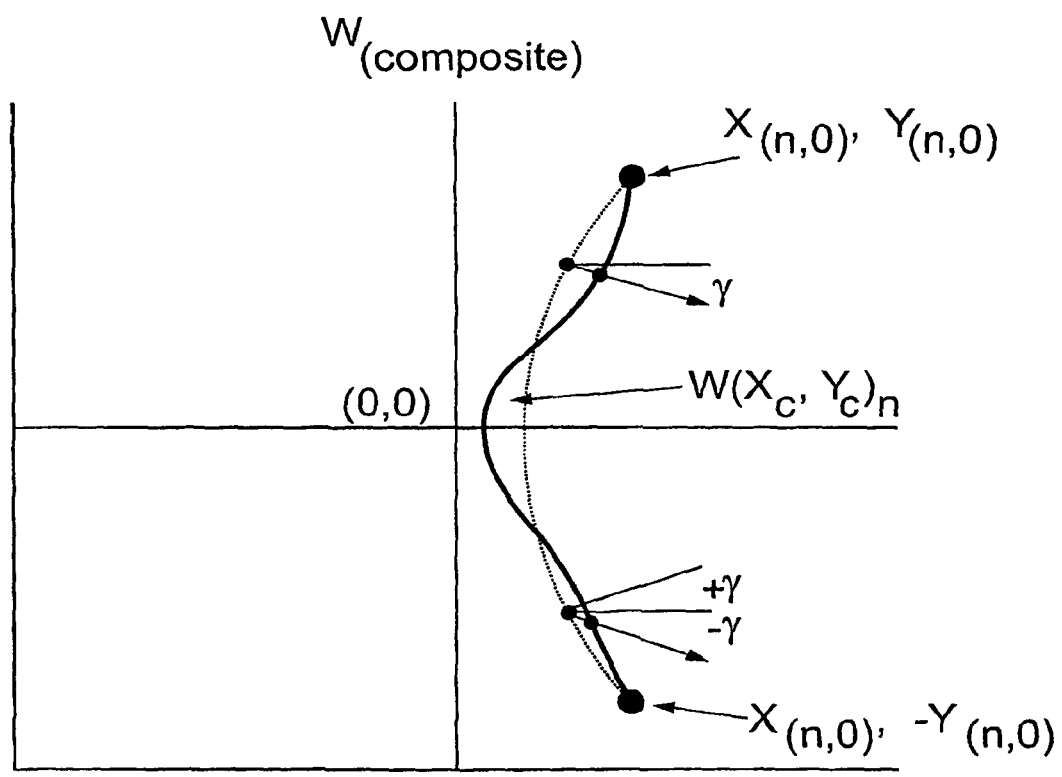
FIG. 17 is a plot of the composite function used in construction of the molded leaflet position P resulting from combining an underlying function (FIG. 15) and an asymmetric superimposed function (FIG. 16) for a valve made in accordance with the second embodiment.

A circular arc is defined by its cord length, $2Y_{(n,O)}$, and amplitude, $A_u$, as shown in FIG. 15. $A_s$ can be varied across the leaflet to produce varying wave amplitude across the leaflet, for example lower amplitude in one commissure than the opposite commissure. $B_s$ can be varied to adjust the length of the wave. The superimposed wave is shown in FIG. 16. The composite wave formed by combining the underlying wave (FIG. 15) with the superimposed wave (FIG. 16) is shown in FIG. 17. The composite wave $W(X_c, Y_c)_n$ is created by offsetting the superimposed wave normal to the surface of the underlying wave (FIG. 17). Positive $\gamma$ is defined as the direction of the normal to the underlying wave relative to the x-axis. When Y is positive, the composite curve is created by offsetting in the direction positive $\gamma$ and where Y is negative the composite curve is created by offsetting in the direction negative $\gamma$ (the offset direction is shown by arrows for a positive Y point and a negative Y point in FIG. 17.

While the general shape of the leaflet in position P has been determined using the composite wave, at this stage it is not specified in any particular position. In order to specify the position of P, the shape of the partially open leaflet position can be defined using the ratio of the amplitude of the circular arc $A_u$ to the amplitude of the sinusoidal wave $B_s$.

A large ratio results in a leaflet which is substantially closed and vice versa. In this example the ratio changes from 10 at the base of the leaflet to 4 at the free edge of the leaflet. The result of this is a leaflet which effectively is more open at the free edge than at the base of the leaflet. In this way, the degree of 'openness' of the leaflet in position P can be varied throughout the leaflet.

The composite wave is thus defined to produce the molded "buckle" in the leaflet, and the amplitude ratio is used to define the geometry of the leaflet at position P. At this stage it may bear no relation to the closed leaflet shape in position C. In order to match the area distribution of both leaflet positions, (thus producing essentially the same leaflet in different positions) the composite wave length is iterated to match the length of the relevant leaflet contour in position C. Thus the amplitude and frequency of the individual waves can be varied in such a manner as to balance between: (a) producing a resultant wave the length of which is equal to the relevant value in the length function $L(Z)$ thus approximating the required closed shape when back pressure is applied, and (b) allowing efficient orifice washout and ready leaflet opening.

This process identifies the values of $A_u$ and $B_S$ to be used in constructing the mold for the valve leaflet. As long as the constants such as $A_u$ and $B_s$ are known, the surface of the leaflet in its molded position can be visualised, enclosed and machined in a conventional manner. As a result of this fitting process the composite wave retains the same basic form but changes in detail from the top of the leaflet to the bottom of the leaflet. A composite wave can be defined in the leaflet surface as the intersection of the leaflet surface with a plane normal to the Z axis.

In summary therefore one possible method of designing the leaflet of the second embodiment of the present invention is in the following way:

(1) Define a scallop shape;
(2) Define a shape representing the closed leaflet using a contour length function L(Z);
(3) Use circular arcs and sine waves to generate a geometry which is partially-open, which pertains to a leaflet position which is between the two extreme conditions of normal valve function, i.e., leaflet open and leaflet closed;
(5) Vary the amplitude of the arcs and the sinewaves to fit to the length function L(Z); and
(6) The respective amplitudes of the circular arcs and sine waves can be varied from the free edge to leaflet base, for example the degree of 'openness' of the leaflet can be varied throughout the leaflet.

Example 3 set forth hereafter is an example of how the invention of the second embodiment can be put into practice. Using the scallop constants in Table 5, the constants required to produce an example of an asymmetric leaflet valve are given in Table 6. These constants are used in conjunction with the aforementioned equations to define the leaflet geometry.

With one leaflet described using the aforementioned equations, the remaining two leaflets are generated by rotating the geometry about the Z axis through 120° and then through 240°. These leaflet shapes are inserted as the areas of the dipping mold (otherwise known as a dipping former), which form the majority of the leaflet forming surfaces, and which then forms a 3-dimensional dipping mold. The composite wave described in the aforementioned equations, therefore substantially defines the former surface which produces the inner leaflet surface. A drain-off area 30 is also created on the former to encourage smooth run-off of polymer solution. The drain-off region 30 is defined by extruding the leaflet free edge away from the leaflet and parallel to the flow direction of the valve for a distance of approximately 10 mm. The transition from leaflet forming surface of the dipping mold 24 to the drain-off surface of the dipping mold 30 is radiused with a radius greater than 1 mm and preferably greater than 2 mm to eliminate discontinuities in the leaflet.

The details of the manufacture of the valve of the second embodiment are similar to those previously described with respect to the valve of the first embodiment until the valve is removed from the dipping mold. Since the former used in making the valve of the second embodiment is not tapered the stent posts are not deflected by the former and do not move or change the leaflet shape when the valve is removed from the mold. At this stage the dipping mold and frame is covered with an excess of polyurethane due to the drain-off of the polymer onto the region of the mold known as the drain-off area 30. To maintain the integrity of the frame coating, the leaflet is trimmed above the stent tips at a distance of between 0.025 to 5 mm preferably 0.5 mm to 1.5 mm from the stent tip. Thus part of the surface of the leaflet is formed on the drain-off region 30 which is substantially defined using the composite wave $W(X_c, Y_c)_0$. Leaflet free edges may be trimmed of excess material using a sharp blade rotated around the opened leaflets or using laser-cutting technology or other similar technology.

The valve of the second embodiment may be used in any required position within the heart to control blood flow in one direction, or to control flow within any type of cardiac assist device.

The following example 3 uses the same scallop geometry described using the constants set forth in Table 5: While the example 3 described herein relates to one valve size, the same method can be used to produce valves from a wide range of sizes. This can be carried out by modifying the constants used in the equations, and computing and iterating in the normal fashion or by resealing the leaflet.

TABLE 5

|  | values (mm) |
| --- | --- |
| R | 11.0 |
| slope | −2.517 |
| intersection | 14.195 |

EXAMPLE 3

The parameters described in the preceding sections are assigned the values set forth in Table 6 and are used to manufacture an asymmetric valve according to the second embodiment. The included angle between adjacent leaflet free edges at the valve commissure for this valve is approximately 30°.

TABLE 6

| Parameter | Value (mm) |
| --- | --- |
|  | Closed position |
| L(Z) | Varies from 0.025 mm at the leaflet base to 21.3 mm at the free edge |
|  | Partially-open position |
| θ | 0° |
| $A_u$ | Result from iteration procedure finds that $A_u$ varies from 0.0006 at the leaflet base to 3.8 at 10.7 mm from the leaflet base to 3.35 at the free edge. |
| $A_s$ | At the free edge of the leaflet, $A_s(Y)$ varies from 1.5 mm at one side of the scallop to 1.0 mm at the opposite side of the scallop. At the base of the leaflet, $A_s(Y)$ is 1.0 mm. |
| $B_s$ | Result from iteration procedure finds that $A_s$ varies from 0.0006 at the leaflet base to 0.839 mm at the free edge. |

Figure 18:
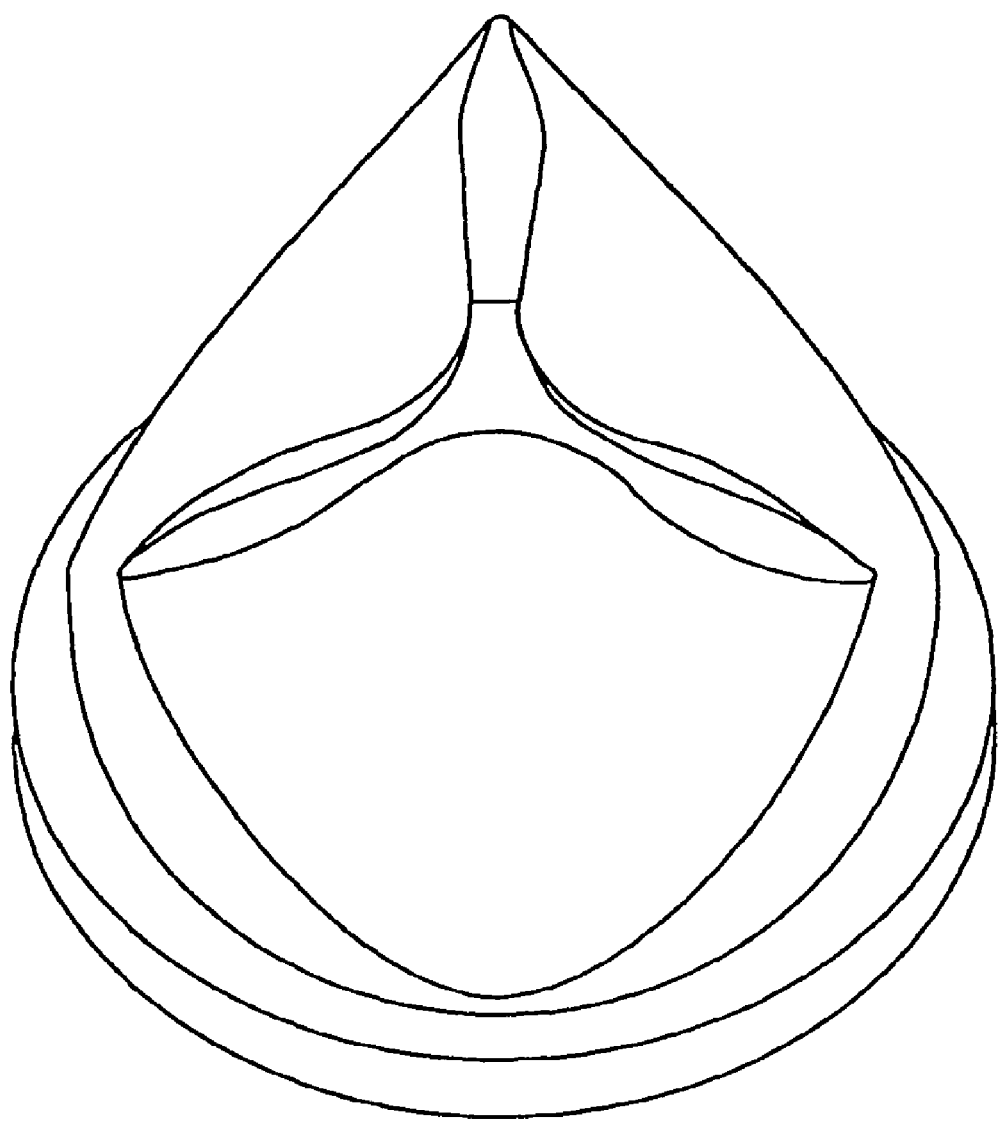
FIG. 18 is a perspective view of a valve of the second embodiment having asymmetric leaflets.

FIG. 18 shows the asymmetric valve which is manufactured, using the values outlined in Table 5 and Table 6.

TABLE 7

| Definition of parameters | |
| --- | --- |
| R | Internal radius of valve Scallop (FIG. 2) |

The scallop is defined using a simple straight line, defined using a slope and intersection, to cut with a cylinder.

Closed Leaflet geometry C

L(Z) is used to modify the inherent geometry of the leaflet. Circular arcs and straight lines can be used to enclose the surface defined using L(Z).

TABLE 7-continued

Definition of parameters

Molded position P

P is enclosed by a number (n) of contours $W(X, Y)_n$ which run from one side of the scallop to the other. The underlying function is used in defining both symmetric and asymmetric leaflets. running in a plane from one side of the scallop to the other. The points on the scallop are designated $X_{(n,0)}$, $Y_{(n,0)}$ where n refers to the contour number (see FIGS. 15, 16, 17, 18).

| | |
|---|---|
| Y | Variable in plane from $Y_{(n,0)}$ to $-Y_{(n,0)}$ |
| $A_u$ | $A_u$ is the amplitude of the underlying wave |
| $A_s(Y)$ | $A_s$ is a function which biases the wave amplitude in a defined way, e.g. the amplitude of the wave can be varied from commissure to commissure to produce asymmetry in the leaflet. |
| $B_s$ | $B_s$ is the amplitude of the superimposed wave |

Composite Curve (FIGS. 17)

| | |
|---|---|
| $X_c$ | X coordinate for defining the composite curve. |
| $Y_c$ | Y coordinate for defining the composite curve. |

Open Leaflet position (FIG. 18)

The open leaflet position is defined using a ratio which determines the degree of "openness" of the leaflet.

| | |
|---|---|
| θ | Former taper angle |

What is claimed is:

1. A method of making a cardiac valve prosthesis which includes a frame defining a blood flow axis substantially parallel to the flow of blood through the valve prosthesis and at least two flexible leaflets attached to the frame, the method comprising:

providing a mold having a cavity sized to accommodate the frame;

inserting the frame into the mold;

inserting the mold into an injection molding machine;

injecting molten polymer into the cavity of the mold to form the at least two leaflets and bond the at least two leaflets to the frame, the cavity being shaped to form the at least two leaflets in a neutral position in a desired configuration, the at least two leaflets being configured to be movable from an open to a closed position, the at least two leaflets having a blood inlet side and a blood outlet side, the at least two leaflets being in the closed position when fluid pressure is applied to the outlet side, being in the open position when fluid pressure is applied to the inlet side and being in a neutral position intermediate the open and closed position in the absence of fluid pressure being applied to the leaflets, the at least two leaflets including a first leaflet having a surface contour such that when the first leaflet is in the neutral position an intersection of the first leaflet with at least one plane perpendicular to the blood flow axis forms a first composite wave, the first composite wave being substantially defined by a first wave combined with at least a second superimposed wave, the first wave having a first frequency, the second wave having a second frequency, the first frequency being different from the second frequency, the first composite wave providing multiple curves in the leaflet free edge, and wherein the frame is substantially cylindrical having first and second ends, one of the ends defining at least two scalloped edge portions separated by at least two posts, each post having a tip, wherein each leaflet has a fixed edge joined to a respective scalloped edge portion of the frame and a free edge extending substantially between the tips of two posts, and wherein when the at least two leaflets are in the neutral position the valve prosthesis has partially open commissures defined by an included angle between adjacent leaflet free edges that is in the range of 10 to 55°.

2. The method of claim 1 wherein the first composite wave formed in the injecting step is defined by a first wave combined with second and third waves superimposed over the first wave, the third wave having a third frequency which is different from the first frequency.

3. The method of claim 1 wherein the first wave in the injecting step is symmetric about a plane parallel to and intersecting the blood flow axis and bisecting the first leaflet.

4. The method of claim 1 wherein the first wave in the injecting step is asymmetric about a plane parallel to and intersecting the blood flow axis and bisecting the first leaflet.

5. The method of claim 1 wherein the second wave in the injecting step is symmetric about a plane parallel to and intersecting the blood flow axis and bisecting the first leaflet.

6. The method of claim 1 wherein the second wave in the injecting step is asymmetric about a plane parallel to and intersecting the blood flow axis and bisecting the first leaflet.

7. The method of claim 3 wherein the second wave in the injecting step is symmetric about a plane parallel to and intersecting the blood flow axis and bisecting the first leaflet.

8. The method of claim 3 wherein the second wave in the injecting step is asymmetric about a plane parallel to and intersecting the blood flow axis and bisecting the first leaflet.

9. The method of claim 4 wherein the second wave in the injecting step is symmetric about a plane parallel to and intersecting the blood flow axis and bisecting the first leaflet.

10. The method of claim 4 wherein the second wave in the injecting step is asymmetric about a plane parallel to and intersecting the blood flow axis and bisecting the first leaflet.

11. The method of claim 1 wherein the first composite wave in the injecting step is asymmetric about a plane parallel to and intersecting the blood flow axis and bisecting the first leaflet.

12. The method of claim 1 wherein the first composite wave in the injecting step is asymmetric about a plane parallel to and intersecting the blood flow axis and bisecting the first leaflet.

13. The method of claim 1 wherein the at least two leaflets formed in the injecting step include second and third leaflets and wherein an intersection of the second and third leaflets with the plane perpendicular to the blood flow axis forms second and third composite waves, respectively, the second and third composite waves being substantially the same as the first composite wave.

14. The method of claim 1 wherein the first wave in the injecting step is defined by an equation which is one of trigonometric, elliptical, hyperbolic, parabolic, circular, a smooth analytic function and a table of values.

15. The method of claim 1 wherein the second wave in the injecting step is defined by an equation which is one of trigonometric, elliptical, hyperbolic, parabolic, circular, a smooth analytic function and a table of values.

16. The method of claim 11 wherein the first and second waves in the injecting step are symmetric about a plane parallel to and intersecting the blood flow axis and bisecting the first leaflet.

17. The method of claim 12 wherein at least one of the first and second waves in the injecting step is asymmetric about a plane parallel to and intersecting the blood flow axis and bisecting the first leaflet.

18. The method of claim 1 wherein the at least two leaflets in the injecting step are configured such that they are substantially free of bending stresses when in the neutral position.

19. The method of claim 1 where the included angle between adjacent leaflet free edges at the partially open commissures is in the range of 25 to 55°.

20. The method of claim 1 where the included angle between adjacent leaflet free edges at the partially open commissures is in the range of 40 to 55°.

* * * * *